US010925651B2

(12) United States Patent
Rush et al.

(10) Patent No.: US 10,925,651 B2
(45) Date of Patent: Feb. 23, 2021

(54) IMPLANT HAVING LOCKING HOLES WITH COLLECTION CAVITY FOR SHAVINGS

(71) Applicant: DePuy Synthes Products, Inc., Raynham, MA (US)

(72) Inventors: Jesse B. Rush, Telford, PA (US); Christopher Keegan, Hatboro, PA (US); Michael McGurk, Williamstown, NJ (US); Simon M. Bosshard, Bern (CH)

(73) Assignee: DePuy Synthes Products, Inc., Raynham, MA (US)

( * ) Notice: Subject to any disclaimer, the term of this patent is extended or adjusted under 35 U.S.C. 154(b) by 81 days.

(21) Appl. No.: 16/230,880

(22) Filed: Dec. 21, 2018

(65) Prior Publication Data

US 2020/0197056 A1 Jun. 25, 2020

(51) Int. Cl.
*A61B 17/80* (2006.01)
*A61B 17/86* (2006.01)
*A61B 17/17* (2006.01)

(52) U.S. Cl.
CPC ...... *A61B 17/8057* (2013.01); *A61B 17/1728* (2013.01); *A61B 17/8061* (2013.01); *A61B 17/8004* (2013.01); *A61B 17/808* (2013.01); *A61B 17/8605* (2013.01)

(58) Field of Classification Search
CPC .. A61B 17/80; A61B 17/8052; A61B 17/8057
See application file for complete search history.

(56) References Cited

U.S. PATENT DOCUMENTS

| 327,296 A | 9/1885 | Mcginnis |
| 1,105,105 A | 7/1914 | Sherman |
| 1,203,546 A | 10/1916 | Parsons |
| 2,228,584 A | 1/1941 | Piace |
| 2,352,297 A | 6/1944 | Wales |
| 2,414,882 A | 1/1947 | Longfellow |
| 2,443,363 A | 6/1948 | Kenneth et al. |
| 2,477,430 A | 7/1949 | Swanstrom |
| 2,496,126 A | 1/1950 | Haboush |
| 2,526,959 A | 10/1950 | Lorenzo |
| 2,612,159 A | 9/1952 | Collison |

(Continued)

FOREIGN PATENT DOCUMENTS

| CA | 1112803 A | 11/1981 |
| CA | 2047521 A1 | 1/1992 |

(Continued)

OTHER PUBLICATIONS

Zimmer Advertisement, J. of Orthopaedic Trauma, vol. 12, No. 5, Jun./Jul. 1998.

(Continued)

*Primary Examiner* — Matthew J Lawson
(74) *Attorney, Agent, or Firm* — BakerHostetler

(57) ABSTRACT

A bone plate includes locking holes that reconfigured to threadedly mate with locking screws to fix the bone plate to an underlying bone. Some of the locking holes are standard-type locking holes. Alternatively or additionally, some of the locking holes are variable-angle locking holes. The bone plate defines a collection cavity in the locking holes that are configured to collect shavings that can be produced if the bone screw is cross threaded in the locking hole.

19 Claims, 7 Drawing Sheets

(56) References Cited

U.S. PATENT DOCUMENTS

| | | |
|---|---|---|
| 2,627,855 A | 2/1953 | Price |
| 2,699,774 A | 1/1955 | Livingston |
| 2,772,676 A | 12/1956 | Pohl |
| 2,801,631 A | 8/1957 | Charnley |
| 2,846,701 A | 8/1958 | Bedford, Jr. |
| 2,874,691 A | 2/1959 | Mason |
| 3,025,853 A | 3/1962 | Mason |
| 3,229,743 A | 1/1966 | Derby |
| 3,263,949 A | 8/1966 | Conrad |
| 3,314,326 A | 4/1967 | Bedford, Jr. |
| 3,364,807 A | 1/1968 | Holton |
| 3,374,786 A | 3/1968 | Callender, Jr. |
| 3,388,732 A | 6/1968 | Holton |
| 3,463,148 A | 8/1969 | Treace |
| 3,489,143 A | 1/1970 | Halloran |
| 3,534,731 A | 10/1970 | Muller |
| 3,551,389 A | 12/1970 | Prince, Jr. |
| 3,552,389 A | 1/1971 | Allgower et al. |
| 3,561,437 A | 2/1971 | Orlich |
| 3,577,601 A | 5/1971 | Mariani et al. |
| 3,630,261 A | 12/1971 | Gley |
| 3,668,972 A | 6/1972 | Allgower et al. |
| 3,688,972 A | 9/1972 | Mahon |
| 3,695,259 A | 10/1972 | Yost |
| 3,695,618 A | 10/1972 | Woolley et al. |
| 3,716,050 A | 2/1973 | Johnston |
| 3,741,205 A | 6/1973 | Markolf et al. |
| 3,744,488 A | 7/1973 | Cox |
| 3,779,240 A | 12/1973 | Kondo |
| 3,782,374 A | 1/1974 | Fischer |
| 3,824,995 A | 7/1974 | Getscher et al. |
| 3,842,825 A | 10/1974 | Wagner |
| 3,877,339 A | 4/1975 | Muenchinger |
| RE28,841 E | 6/1976 | Martin et al. |
| 3,967,049 A | 6/1976 | Brandt |
| 3,996,834 A | 12/1976 | Reynolds |
| 3,996,931 A | 12/1976 | Callender, Jr. |
| 4,009,712 A | 3/1977 | Burstein et al. |
| 4,029,091 A | 6/1977 | Von et al. |
| 4,040,129 A | 8/1977 | Steinemann et al. |
| 4,095,591 A | 6/1978 | Graham et al. |
| 4,120,298 A | 10/1978 | Fixel |
| 4,172,452 A | 10/1979 | Forte et al. |
| 4,175,555 A | 11/1979 | Herbert |
| 4,219,015 A | 8/1980 | Steinemann |
| 4,236,512 A | 12/1980 | Aginsky |
| 4,263,904 A | 4/1981 | Judet |
| 4,269,180 A | 5/1981 | Dall et al. |
| 4,304,039 A | 12/1981 | Asmus |
| 4,338,926 A | 7/1982 | Kummer et al. |
| 4,355,198 A | 10/1982 | Gartland, Jr. |
| 4,379,451 A | 4/1983 | Getscher |
| 4,388,921 A | 6/1983 | Sutter et al. |
| 4,408,601 A | 10/1983 | Wenk |
| 4,429,690 A | 2/1984 | Angelino-Pievani |
| 4,438,762 A | 3/1984 | Kyle |
| 4,454,876 A | 6/1984 | Mears |
| RE31,628 E | 7/1984 | Allgower et al. |
| 4,484,570 A | 11/1984 | Sutter et al. |
| 4,484,750 A | 11/1984 | Scruggs |
| 4,488,543 A | 12/1984 | Tornier |
| 4,491,317 A | 1/1985 | Bansal |
| 4,493,317 A | 1/1985 | Klaue |
| 4,494,535 A | 1/1985 | Haig |
| 4,513,744 A | 4/1985 | Klaue |
| 4,537,185 A | 8/1985 | Stednitz |
| 4,565,193 A | 1/1986 | Streli |
| 4,580,225 A | 4/1986 | Thompson |
| 4,612,920 A | 9/1986 | Lower |
| 4,612,923 A | 9/1986 | Kronenthal |
| 4,616,638 A | 10/1986 | Griggs |
| 4,617,922 A | 10/1986 | Griggs |
| 4,621,629 A | 11/1986 | Koeneman |
| 4,628,923 A | 12/1986 | Medoff |
| 4,629,455 A | 12/1986 | Kanno |
| 4,630,985 A | 12/1986 | Simons |
| 4,651,724 A | 3/1987 | Berentey et al. |
| 4,657,001 A | 4/1987 | Fixel |
| 4,683,878 A | 8/1987 | Carter |
| 4,717,613 A | 1/1988 | Ottaviano |
| 4,747,613 A | 5/1988 | Brichoud et al. |
| 4,776,329 A | 10/1988 | Treharne |
| 4,776,330 A | 10/1988 | Chapman et al. |
| 4,781,183 A | 11/1988 | Casey et al. |
| 4,791,918 A | 12/1988 | Von Hasselbach |
| 4,794,918 A | 1/1989 | Wolter |
| 4,795,473 A | 1/1989 | Grimes |
| 4,800,874 A | 1/1989 | David et al. |
| 4,838,252 A | 6/1989 | Klaue |
| 4,848,328 A | 7/1989 | Laboureau et al. |
| 4,858,601 A | 8/1989 | Glisson |
| 4,867,144 A | 9/1989 | Karas et al. |
| 4,903,691 A | 2/1990 | Heinl |
| 4,905,680 A | 3/1990 | Tunc |
| 4,927,421 A | 5/1990 | Goble et al. |
| 4,955,886 A | 9/1990 | Pawluk |
| 4,957,496 A | 9/1990 | Schmidt |
| 4,957,497 A | 9/1990 | Hoogland et al. |
| 4,964,403 A | 10/1990 | Karas et al. |
| 4,966,599 A | 10/1990 | Pollock |
| 4,973,332 A | 11/1990 | Kummer |
| 4,973,333 A | 11/1990 | Treharne |
| 4,988,350 A | 1/1991 | Herzberg |
| 5,002,544 A | 3/1991 | Klaue et al. |
| 5,006,120 A | 4/1991 | Carter |
| 5,013,313 A | 5/1991 | Surer |
| 5,013,315 A | 5/1991 | Barrows |
| 5,015,248 A | 5/1991 | Burstein et al. |
| 5,027,904 A | 7/1991 | Miller et al. |
| 5,039,265 A | 8/1991 | Rath et al. |
| 5,041,113 A | 8/1991 | Biedermann et al. |
| 5,041,114 A | 8/1991 | Chapman et al. |
| 5,041,116 A | 8/1991 | Wilson |
| 5,053,036 A | 10/1991 | Perren et al. |
| 5,085,660 A | 2/1992 | Lin |
| 5,087,260 A | 2/1992 | Fixel |
| 5,108,399 A | 4/1992 | Eitenmuller et al. |
| 5,108,449 A | 4/1992 | Gray |
| 5,116,336 A | 5/1992 | Frigg |
| 5,127,914 A | 7/1992 | Calderale et al. |
| 5,129,901 A | 7/1992 | Decoste |
| 5,139,497 A | 8/1992 | Tilghman et al. |
| 5,147,361 A | 9/1992 | Ojima et al. |
| 5,147,363 A | 9/1992 | Haerle |
| 5,151,103 A | 9/1992 | Tepic et al. |
| 5,152,794 A | 10/1992 | Davidson |
| 5,190,544 A | 3/1993 | Chapman et al. |
| 5,197,966 A | 3/1993 | Sommerkamp |
| 5,201,733 A | 4/1993 | Etheredge, III |
| 5,261,910 A | 11/1993 | Warden et al. |
| 5,269,784 A | 12/1993 | Mast |
| 5,275,601 A | 1/1994 | Gogolewski et al. |
| 5,290,281 A | 3/1994 | Tschakaloff |
| 5,300,074 A | 4/1994 | Frigg |
| 5,304,180 A | 4/1994 | Slocum |
| 5,306,275 A | 4/1994 | Bryan |
| 5,324,290 A | 6/1994 | Zdeblick et al. |
| 5,324,292 A | 6/1994 | Meyers |
| 5,336,224 A | 8/1994 | Selman |
| 5,356,410 A | 10/1994 | Pennig |
| 5,360,429 A | 11/1994 | Jeanson et al. |
| 5,360,448 A | 11/1994 | Thramann |
| 5,364,398 A | 11/1994 | Chapman et al. |
| 5,364,399 A | 11/1994 | Lowery et al. |
| 5,372,598 A | 12/1994 | Luhr et al. |
| 5,376,126 A | 12/1994 | Lin |
| 5,395,372 A | 3/1995 | Holt et al. |
| 5,403,136 A | 4/1995 | Mathys |
| 5,413,577 A | 5/1995 | Pollock |
| 5,429,641 A | 7/1995 | Gotfried |
| 5,433,719 A | 7/1995 | Pennig |
| 5,458,654 A | 10/1995 | Tepic |
| 5,462,547 A | 10/1995 | Weigum |
| 5,484,439 A | 1/1996 | Olson et al. |

(56) References Cited

U.S. PATENT DOCUMENTS

| | | |
|---|---|---|
| 5,514,138 A | 5/1996 | McCarthy |
| 5,520,690 A | 5/1996 | Errico et al. |
| 5,522,902 A | 6/1996 | Yuan et al. |
| 5,531,746 A | 7/1996 | Errico et al. |
| 5,534,032 A | 7/1996 | Hodorek |
| 5,558,674 A | 9/1996 | Heggeness et al. |
| 5,569,248 A | 10/1996 | Mathews |
| 5,571,109 A | 11/1996 | Bertagnoli |
| 5,571,198 A | 11/1996 | Drucker et al. |
| 5,586,985 A | 12/1996 | Putnam et al. |
| 5,591,168 A | 1/1997 | Judet et al. |
| 5,601,551 A | 2/1997 | Taylor et al. |
| 5,601,553 A | 2/1997 | Trebing et al. |
| 5,607,426 A | 3/1997 | Ralph et al. |
| 5,607,427 A | 3/1997 | Tschakaloff |
| 5,607,428 A | 3/1997 | Lin |
| 5,620,445 A | 4/1997 | Brosnahan et al. |
| 5,647,872 A | 7/1997 | Gilbert et al. |
| 5,655,089 A | 8/1997 | Bucci |
| 5,658,339 A | 8/1997 | Tronzo et al. |
| 5,662,655 A | 9/1997 | Laboureau et al. |
| 5,674,222 A | 10/1997 | Berger et al. |
| 5,676,667 A | 10/1997 | Hausman |
| 5,681,311 A | 10/1997 | Foley et al. |
| D385,963 S | 11/1997 | Hansson |
| 5,690,633 A | 11/1997 | Taylor et al. |
| 5,693,055 A | 12/1997 | Zahiri et al. |
| 5,702,396 A | 12/1997 | Hoenig et al. |
| 5,702,399 A | 12/1997 | Kilpela et al. |
| 5,709,682 A | 1/1998 | Medoff |
| 5,709,686 A | 1/1998 | Talos et al. |
| 5,709,687 A | 1/1998 | Pennig |
| 5,718,704 A | 2/1998 | Medoff |
| 5,718,705 A | 2/1998 | Sammarco |
| 5,728,099 A | 3/1998 | Tellman et al. |
| 5,733,287 A | 3/1998 | Tepic et al. |
| 5,735,853 A | 4/1998 | Olerud |
| 5,741,256 A | 4/1998 | Bresina |
| 5,741,258 A | 4/1998 | Klaue et al. |
| 5,743,912 A | 4/1998 | Lahille et al. |
| 5,749,872 A | 5/1998 | Kyle et al. |
| 5,766,175 A | 6/1998 | Martinotti |
| 5,772,662 A | 6/1998 | Chapman et al. |
| 5,779,706 A | 7/1998 | Tschakaloff |
| 5,785,713 A | 7/1998 | Jobe |
| 5,797,916 A | 8/1998 | McDowell |
| 5,800,553 A | 9/1998 | Albrektsson et al. |
| 5,810,821 A | 9/1998 | Vandewalle |
| 5,810,822 A | 9/1998 | Mortier |
| 5,810,823 A | 9/1998 | Klaue et al. |
| 5,827,286 A | 10/1998 | Incavo et al. |
| 5,853,413 A | 12/1998 | Carter et al. |
| 5,921,988 A | 7/1999 | Legrand |
| 5,928,084 A | 7/1999 | Green |
| 5,931,801 A | 8/1999 | Burbank et al. |
| 5,931,839 A | 8/1999 | Medoff |
| 5,938,664 A | 8/1999 | Winquist et al. |
| 5,954,722 A | 9/1999 | Bono |
| 5,961,524 A | 10/1999 | Crombie |
| 5,968,046 A | 10/1999 | Castleman |
| 5,968,047 A | 10/1999 | Reed |
| 5,973,223 A | 10/1999 | Tellman et al. |
| 5,976,139 A | 11/1999 | Bramlet |
| 5,976,141 A | 11/1999 | Haag et al. |
| 5,989,255 A | 11/1999 | Pepper et al. |
| 5,999,940 A | 12/1999 | Ranger |
| 6,001,099 A | 12/1999 | Huebner |
| 6,007,535 A | 12/1999 | Rayhack et al. |
| 6,022,352 A | 2/2000 | Vandewalle |
| 6,030,162 A | 2/2000 | Huebner |
| 6,030,389 A | 2/2000 | Wagner et al. |
| 6,059,785 A | 5/2000 | Schavan et al. |
| 6,066,141 A | 5/2000 | Dall et al. |
| 6,096,040 A | 8/2000 | Esser |
| 6,113,603 A | 9/2000 | Medoff |
| 6,129,728 A | 10/2000 | Schumacher et al. |
| 6,129,730 A | 10/2000 | Bono et al. |
| 6,152,927 A | 11/2000 | Farris et al. |
| 6,155,756 A | 12/2000 | Mericle et al. |
| 6,183,474 B1 | 2/2001 | Bramlet et al. |
| 6,183,475 B1 | 2/2001 | Lester et al. |
| 6,187,007 B1 | 2/2001 | Frigg et al. |
| 6,206,881 B1 | 3/2001 | Frigg et al. |
| 6,221,073 B1 | 4/2001 | Weiss et al. |
| 6,221,075 B1 | 4/2001 | Toermala et al. |
| D443,060 S | 5/2001 | Benirschke et al. |
| 6,224,602 B1 | 5/2001 | Hayes |
| 6,228,085 B1 | 5/2001 | Theken et al. |
| 6,235,032 B1 | 5/2001 | Link |
| 6,235,033 B1 | 5/2001 | Brace et al. |
| 6,258,250 B1 | 7/2001 | Weissenbacher et al. |
| 6,261,291 B1 | 7/2001 | Talaber et al. |
| 6,283,969 B1 | 9/2001 | Grusin et al. |
| 6,287,309 B1 | 9/2001 | Baccelli et al. |
| 6,290,703 B1 | 9/2001 | Ganem |
| 6,306,136 B1 | 10/2001 | Baccelli |
| 6,306,140 B1 | 10/2001 | Siddiqui |
| 6,322,562 B1 | 11/2001 | Wolter |
| 6,325,803 B1 | 12/2001 | Schumacher et al. |
| 6,338,734 B1 | 1/2002 | Burke et al. |
| 6,342,055 B1 | 1/2002 | Eisermann et al. |
| 6,348,052 B1 | 2/2002 | Sammarco |
| 6,350,265 B1 | 2/2002 | Blaustein et al. |
| 6,355,041 B1 | 3/2002 | Martin |
| 6,355,042 B2 | 3/2002 | Winquist et al. |
| 6,358,250 B1 | 3/2002 | Orbay |
| 6,364,882 B1 | 4/2002 | Orbay |
| 6,375,657 B1 | 4/2002 | Doubler et al. |
| 6,379,359 B1 | 4/2002 | Dahners |
| D458,374 S | 6/2002 | Bryant et al. |
| D458,683 S | 6/2002 | Bryant et al. |
| D458,684 S | 6/2002 | Bryant et al. |
| D458,996 S | 6/2002 | Bryant et al. |
| 6,423,064 B1 | 7/2002 | Kluger |
| 6,440,131 B1 | 8/2002 | Haidukewych |
| 6,440,135 B2 | 8/2002 | Orbay et al. |
| D463,557 S | 9/2002 | Bryant et al. |
| D463,558 S | 9/2002 | Bryant et al. |
| D463,559 S | 9/2002 | Bryant et al. |
| 6,454,769 B2 | 9/2002 | Wagner et al. |
| 6,454,770 B1 | 9/2002 | Klaue |
| D464,136 S | 10/2002 | Bryant et al. |
| D464,731 S | 10/2002 | Bryant et al. |
| 6,468,278 B1 | 10/2002 | Mueckter |
| 6,488,685 B1 | 12/2002 | Manderson |
| D469,532 S | 1/2003 | Bryant et al. |
| D469,533 S | 1/2003 | Bryant et al. |
| D469,534 S | 1/2003 | Bryant et al. |
| 6,503,252 B2 | 1/2003 | Hansson |
| 6,503,281 B1 | 1/2003 | Mallory |
| 6,508,819 B1 | 1/2003 | Orbay |
| D469,874 S | 2/2003 | Bryant et al. |
| D469,875 S | 2/2003 | Bryant et al. |
| D470,588 S | 2/2003 | Bryant et al. |
| 6,525,525 B1 | 2/2003 | Azinger |
| 6,527,776 B1 | 3/2003 | Michelson |
| 6,533,789 B1 | 3/2003 | Hall et al. |
| 6,565,525 B1 | 5/2003 | Burbank et al. |
| 6,565,569 B1 | 5/2003 | Assaker et al. |
| 6,575,975 B2 | 6/2003 | Brace et al. |
| 6,602,256 B1 | 8/2003 | Hayes |
| 6,605,090 B1 | 8/2003 | Trieu et al. |
| D479,331 S | 9/2003 | Pike et al. |
| D480,141 S | 9/2003 | Benirschke et al. |
| 6,623,486 B1 | 9/2003 | Weaver et al. |
| 6,648,891 B2 | 11/2003 | Kim |
| 6,666,868 B2 | 12/2003 | Fallin |
| 6,669,700 B1 | 12/2003 | Farris et al. |
| 6,669,701 B2 | 12/2003 | Steiner et al. |
| 6,712,820 B2 | 3/2004 | Orbay |
| 6,719,759 B2 | 4/2004 | Wagner et al. |
| 6,730,091 B1 | 5/2004 | Pfefferle et al. |
| 6,767,351 B2 | 7/2004 | Orbay et al. |
| 6,835,197 B2 | 12/2004 | Roth et al. |

(56) References Cited

U.S. PATENT DOCUMENTS

| | | |
|---|---|---|
| 6,863,483 B2 | 3/2005 | Koenig et al. |
| 6,866,665 B2 | 3/2005 | Orbay |
| 6,875,215 B2 | 4/2005 | Taras et al. |
| 6,893,443 B2 | 5/2005 | Frigg et al. |
| 6,955,677 B2 | 10/2005 | Dahners |
| 6,974,461 B1 | 12/2005 | Wolter |
| 7,001,388 B2 | 2/2006 | Orbay et al. |
| 7,044,953 B2 | 5/2006 | Capanni |
| 7,128,744 B2 | 10/2006 | Weaver et al. |
| 7,169,149 B1 | 1/2007 | Hajianpour |
| 7,179,260 B2 | 2/2007 | Gerlach et al. |
| 7,229,445 B2 | 6/2007 | Hayeck et al. |
| 7,282,053 B2 | 10/2007 | Orbay |
| 7,294,130 B2 | 11/2007 | Orbay |
| 7,309,340 B2 | 12/2007 | Fallin et al. |
| 7,316,687 B2 | 1/2008 | Aikins et al. |
| 7,338,491 B2 | 3/2008 | Baker et al. |
| 7,341,589 B2 | 3/2008 | Weaver et al. |
| 7,354,441 B2 | 4/2008 | Frigg |
| 7,517,350 B2 | 4/2009 | Weiner et al. |
| 7,527,639 B2 | 5/2009 | Orbay et al. |
| 7,537,596 B2 | 5/2009 | Jensen |
| 7,635,381 B2 | 12/2009 | Orbay |
| 7,637,928 B2 | 12/2009 | Fernandez |
| 7,641,677 B2 | 1/2010 | Weiner et al. |
| 7,695,472 B2 | 4/2010 | Young |
| 7,695,502 B2 | 4/2010 | Orbay et al. |
| 7,766,916 B2 | 8/2010 | Leyden et al. |
| 7,771,433 B2 | 8/2010 | Orbay et al. |
| 7,771,457 B2 | 8/2010 | Kay et al. |
| 7,776,076 B2 | 8/2010 | Grady et al. |
| 7,776,916 B2 | 8/2010 | Freeman et al. |
| 7,857,838 B2 | 12/2010 | Orbay |
| 7,867,260 B2 | 1/2011 | Meyer et al. |
| 7,905,909 B2 | 3/2011 | Orbay et al. |
| 7,951,176 B2 | 5/2011 | Grady et al. |
| 8,075,561 B2 | 12/2011 | Wolter |
| 8,092,505 B2 | 1/2012 | Sommers |
| 8,118,846 B2 | 2/2012 | Leither et al. |
| 8,118,848 B2 | 2/2012 | Ducharme et al. |
| 8,337,535 B2 | 12/2012 | White et al. |
| 8,343,196 B2 | 1/2013 | Schneider |
| 8,403,967 B2 | 3/2013 | Orbay |
| 8,506,607 B2 | 8/2013 | Eckhof et al. |
| 8,518,042 B2 | 8/2013 | Winslow et al. |
| 8,556,945 B2 | 10/2013 | Orbay |
| 8,574,268 B2 | 11/2013 | Chan et al. |
| 8,579,946 B2 | 11/2013 | Orbay |
| 8,641,744 B2 | 2/2014 | Weaver et al. |
| 8,758,346 B2 | 6/2014 | Koay et al. |
| 8,814,918 B2 | 8/2014 | Orbay et al. |
| 8,845,698 B2 | 9/2014 | Schneider |
| 8,852,245 B2 | 10/2014 | Schneider |
| 8,876,873 B2 | 11/2014 | Schneider |
| 8,894,693 B2 | 11/2014 | Petit et al. |
| 8,940,029 B2 | 1/2015 | Leung et al. |
| 9,072,558 B2 | 7/2015 | Orbay |
| 9,107,711 B2 | 8/2015 | Hainard |
| 9,168,075 B2 | 10/2015 | Dell Oca |
| 9,265,542 B2 | 2/2016 | Koay et al. |
| 9,277,947 B2 | 3/2016 | Koay et al. |
| 9,295,505 B2 | 3/2016 | Schneider |
| 9,308,034 B2 | 4/2016 | Grady |
| 9,314,284 B2 | 4/2016 | Chan et al. |
| 9,387,022 B2 | 7/2016 | Koay |
| 9,433,454 B2 | 9/2016 | Paolino et al. |
| 9,498,267 B2 | 11/2016 | Pfeiffer et al. |
| 9,510,880 B2 | 12/2016 | Terrill et al. |
| 9,554,909 B2 | 1/2017 | Donner et al. |
| 9,855,083 B2 | 1/2018 | Mighell et al. |
| 9,867,643 B2 | 1/2018 | Terrill et al. |
| 9,931,148 B2 | 4/2018 | Grady |
| 2001/0000186 A1 | 4/2001 | Bramlet et al. |
| 2001/0011172 A1 | 8/2001 | Orbay et al. |
| 2001/0012940 A1 | 8/2001 | Tunc |
| 2002/0013587 A1 | 1/2002 | Winquist et al. |
| 2002/0032446 A1 | 3/2002 | Orbay |
| 2002/0045901 A1 | 4/2002 | Wagner et al. |
| 2002/0049445 A1 | 4/2002 | Hall et al. |
| 2002/0062127 A1 | 5/2002 | Schumacher et al. |
| 2002/0065516 A1 | 5/2002 | Winquist et al. |
| 2002/0128654 A1 | 9/2002 | Steger et al. |
| 2002/0143337 A1 | 10/2002 | Orbay et al. |
| 2002/0143338 A1 | 10/2002 | Orbay et al. |
| 2002/0156474 A1 | 10/2002 | Inack et al. |
| 2002/0183752 A1 | 12/2002 | Steiner et al. |
| 2002/0183753 A1 | 12/2002 | Manderson |
| 2003/0040748 A1 | 2/2003 | Aikins et al. |
| 2003/0055435 A1 | 3/2003 | Barrick |
| 2003/0060827 A1 | 3/2003 | Coughlin |
| 2003/0083660 A1 | 5/2003 | Orbay |
| 2003/0083661 A1 | 5/2003 | Orbay et al. |
| 2003/0105461 A1 | 6/2003 | Putnam |
| 2003/0125738 A1 | 7/2003 | Khanna |
| 2003/0135212 A1 | 7/2003 | Y Chow |
| 2003/0135216 A1 | 7/2003 | Sevrain |
| 2004/0030339 A1 | 2/2004 | Wack et al. |
| 2004/0049193 A1 | 3/2004 | Capanni |
| 2004/0059334 A1 | 3/2004 | Weaver et al. |
| 2004/0059335 A1 | 3/2004 | Weaver et al. |
| 2004/0073218 A1* | 4/2004 | Dahners .............. A61B 17/8057 606/287 |
| 2004/0097937 A1 | 5/2004 | Pike et al. |
| 2004/0097941 A1 | 5/2004 | Weiner et al. |
| 2004/0111089 A1 | 6/2004 | Stevens et al. |
| 2004/0215198 A1 | 10/2004 | Marnay et al. |
| 2004/0254579 A1 | 12/2004 | Buhren et al. |
| 2004/0260291 A1 | 12/2004 | Jensen |
| 2004/0260306 A1 | 12/2004 | Fallin et al. |
| 2005/0015089 A1 | 1/2005 | Young et al. |
| 2005/0049593 A1 | 3/2005 | Duong et al. |
| 2005/0080421 A1 | 4/2005 | Weaver et al. |
| 2005/0085818 A1 | 4/2005 | Huebner |
| 2005/0107796 A1 | 5/2005 | Gerlach et al. |
| 2005/0165400 A1 | 7/2005 | Fernandez |
| 2005/0171544 A1 | 8/2005 | Falkner, Jr. |
| 2005/0187555 A1 | 8/2005 | Biedermann et al. |
| 2005/0216001 A1 | 9/2005 | David |
| 2005/0261688 A1 | 11/2005 | Grady et al. |
| 2005/0277937 A1 | 12/2005 | Leung et al. |
| 2006/0004361 A1 | 1/2006 | Hayeck et al. |
| 2006/0009771 A1 | 1/2006 | Orbay et al. |
| 2006/0058797 A1 | 3/2006 | Mathieu et al. |
| 2006/0200151 A1 | 9/2006 | Ducharme et al. |
| 2006/0217722 A1 | 9/2006 | Dutoit et al. |
| 2006/0235400 A1 | 10/2006 | Schneider |
| 2006/0264946 A1 | 11/2006 | Young |
| 2007/0016205 A1 | 1/2007 | Beutter et al. |
| 2007/0083207 A1 | 4/2007 | Ziolo et al. |
| 2007/0088360 A1* | 4/2007 | Orbay .................. A61B 17/8057 606/287 |
| 2007/0162016 A1 | 7/2007 | Matityahu |
| 2007/0206244 A1 | 9/2007 | Kobayashi |
| 2007/0208378 A1 | 9/2007 | Bonutti et al. |
| 2007/0225716 A1 | 9/2007 | Deffenbaugh et al. |
| 2007/0260244 A1 | 11/2007 | Wolter |
| 2007/0276386 A1 | 11/2007 | Gerlach et al. |
| 2007/0276402 A1 | 11/2007 | Frankel et al. |
| 2008/0065070 A1 | 3/2008 | Freid et al. |
| 2008/0132960 A1 | 6/2008 | Weaver et al. |
| 2008/0140130 A1 | 6/2008 | Chan et al. |
| 2008/0208259 A1 | 8/2008 | Gilbert et al. |
| 2008/0234749 A1* | 9/2008 | Forstein ............. A61B 17/8057 606/291 |
| 2008/0234752 A1 | 9/2008 | Dahners |
| 2008/0300637 A1 | 12/2008 | Austin et al. |
| 2009/0018557 A1 | 1/2009 | Pisharodi |
| 2009/0018588 A1 | 1/2009 | Eckhof et al. |
| 2009/0036933 A1 | 2/2009 | Dube et al. |
| 2009/0076553 A1 | 3/2009 | Wolter |
| 2009/0076554 A1 | 3/2009 | Huebner et al. |
| 2009/0099610 A1 | 4/2009 | Johnson et al. |
| 2009/0118768 A1 | 5/2009 | Sixto et al. |
| 2009/0143824 A1 | 6/2009 | Austin et al. |

(56) References Cited

U.S. PATENT DOCUMENTS

| | | |
|---|---|---|
| 2009/0143825 A1 | 6/2009 | Graham et al. |
| 2009/0216242 A1 | 8/2009 | Riemer et al. |
| 2009/0281543 A1 | 11/2009 | Orbay et al. |
| 2009/0287258 A1 | 11/2009 | Vannemreddy |
| 2009/0292318 A1 | 11/2009 | White et al. |
| 2009/0312803 A1* | 12/2009 | Austin ............ A61B 17/8014 606/305 |
| 2010/0016858 A1 | 1/2010 | Michel |
| 2010/0030277 A1 | 2/2010 | Haidukewych et al. |
| 2010/0057086 A1 | 3/2010 | Price et al. |
| 2010/0076496 A1 | 3/2010 | Fernandez |
| 2010/0094357 A1 | 4/2010 | Wallenstein et al. |
| 2010/0100134 A1 | 4/2010 | Mocanu |
| 2010/0137919 A1* | 6/2010 | Wolter ............ A61B 17/8605 606/308 |
| 2010/0274296 A1 | 10/2010 | Appenzeller et al. |
| 2010/0312285 A1 | 12/2010 | White et al. |
| 2010/0312286 A1 | 12/2010 | Dell Oca |
| 2011/0046681 A1 | 2/2011 | Prandi et al. |
| 2011/0087229 A1 | 4/2011 | Kubiak et al. |
| 2011/0106081 A1 | 5/2011 | Graham et al. |
| 2011/0224671 A1 | 9/2011 | Koay et al. |
| 2011/0301608 A1 | 12/2011 | Roth et al. |
| 2012/0143193 A1 | 6/2012 | Hulliger |
| 2012/0197307 A1 | 8/2012 | Fritzinger et al. |
| 2012/0245642 A1 | 9/2012 | Giannoudis et al. |
| 2013/0096631 A1* | 4/2013 | Leung ............ A61B 17/8605 606/286 |
| 2013/0116735 A1 | 5/2013 | Schneider |
| 2013/0172943 A1 | 7/2013 | Austin et al. |
| 2013/0190828 A1 | 7/2013 | Schneider |
| 2013/0197589 A1 | 8/2013 | Schneider |
| 2013/0245699 A1 | 9/2013 | Orbay et al. |
| 2013/0261675 A1 | 10/2013 | Fritzinger |
| 2014/0005728 A1* | 1/2014 | Koay ............ A61B 17/866 606/281 |
| 2014/0018862 A1 | 1/2014 | Koay et al. |
| 2014/0180345 A1 | 6/2014 | Chan et al. |
| 2014/0207194 A1 | 7/2014 | Wolter |
| 2014/0236154 A1 | 8/2014 | Liao et al. |
| 2014/0271028 A1 | 9/2014 | Arnett |
| 2014/0277180 A1 | 9/2014 | Paolino et al. |
| 2014/0316473 A1 | 10/2014 | Pfeiffer et al. |
| 2014/0324108 A1 | 10/2014 | Orbay et al. |
| 2015/0051651 A1 | 2/2015 | Terrill et al. |
| 2015/0105829 A1 | 4/2015 | Laird |
| 2015/0257802 A1 | 9/2015 | Wolf et al. |
| 2015/0327897 A1 | 11/2015 | Hulliger |
| 2015/0327898 A1 | 11/2015 | Martin |
| 2015/0359575 A1 | 12/2015 | Pech et al. |
| 2016/0074081 A1 | 3/2016 | Weaver et al. |
| 2016/0089191 A1 | 3/2016 | Pak et al. |
| 2016/0143676 A1 | 5/2016 | Koay et al. |
| 2016/0166294 A1 | 6/2016 | Schneider |
| 2016/0242829 A1 | 8/2016 | Kim et al. |
| 2016/0278826 A1 | 9/2016 | Epperly |
| 2016/0310184 A1 | 10/2016 | Kazanovicz et al. |
| 2016/0317205 A1 | 11/2016 | Baker |
| 2016/0367299 A1 | 12/2016 | Paolino et al. |
| 2017/0265915 A1* | 9/2017 | Langdale ............ A61B 17/725 |
| 2017/0319248 A1 | 11/2017 | Milella et al. |
| 2018/0008326 A1 | 1/2018 | Hulliger et al. |
| 2018/0036049 A1* | 2/2018 | Kobayashi ......... A61B 17/8605 |
| 2018/0064476 A1 | 3/2018 | Lopez et al. |
| 2018/0064477 A1* | 3/2018 | Lopez ............ A61B 17/8061 |
| 2018/0064479 A1 | 3/2018 | Lopez et al. |
| 2018/0132913 A1* | 5/2018 | Davison ............ A61B 17/808 |
| 2018/0235681 A1* | 8/2018 | Chambers .......... A61B 17/8605 |
| 2019/0290338 A1* | 9/2019 | Bosshard ............ A61B 17/8047 |
| 2019/0298426 A1 | 10/2019 | Bosshard et al. |

FOREIGN PATENT DOCUMENTS

| | | |
|---|---|---|
| CA | 2536960 A1 | 3/2005 |
| CH | 611147 A5 | 5/1979 |
| CH | 670755 A5 | 7/1989 |
| CH | 672245 A5 | 11/1989 |
| CH | 675531 A5 | 10/1990 |
| CN | 1486162 A | 3/2004 |
| DE | 2933637 A1 | 4/1980 |
| DE | 3442004 C1 | 4/1986 |
| DE | 3722852 A1 | 1/1989 |
| DE | 3743638 A1 | 7/1989 |
| DE | 4004941 A1 | 8/1990 |
| DE | 3942326 A1 | 6/1991 |
| DE | 4201531 A1 | 7/1993 |
| DE | 4341980 A1 | 6/1995 |
| DE | 4343117 A1 | 6/1995 |
| DE | 4438264 A1 | 3/1996 |
| DE | 19636733 A1 | 4/1997 |
| DE | 19629011 A1 | 1/1998 |
| DE | 9321544 U1 | 9/1999 |
| DE | 19832513 A1 | 2/2000 |
| DE | 19858889 A1 | 6/2000 |
| DE | 10015734 A1 | 9/2001 |
| DE | 10125092 A1 | 12/2001 |
| DE | 20309361 U1 | 9/2003 |
| DE | 20317651 U1 | 3/2004 |
| DE | 10319781 B3 | 8/2004 |
| DE | 102004009429 A1 | 9/2005 |
| DE | 102005042766 A1 | 1/2007 |
| DE | 202006019220 U1 | 5/2007 |
| DE | 202008000914 U1 | 3/2008 |
| DE | 202007017159 U1 | 5/2008 |
| DE | 102010048052 | 4/2012 |
| DE | 102016112845 A1 | 1/2018 |
| DE | 202014011161 U1 | 3/2018 |
| EP | 0053999 A1 | 6/1982 |
| EP | 0158030 A1 | 10/1985 |
| EP | 0180532 A1 | 5/1986 |
| EP | 0207884 A2 | 1/1987 |
| EP | 0241914 A2 | 10/1987 |
| EP | 0244782 A1 | 11/1987 |
| EP | 0251583 A2 | 1/1988 |
| EP | 0266146 A2 | 5/1988 |
| EP | 0274713 A1 | 7/1988 |
| EP | 0290138 A2 | 11/1988 |
| EP | 0291632 A1 | 11/1988 |
| EP | 0299160 A1 | 1/1989 |
| EP | 0337288 A1 | 10/1989 |
| EP | 0360139 A2 | 3/1990 |
| EP | 0381462 A2 | 8/1990 |
| EP | 0382256 A1 | 8/1990 |
| EP | 0410309 A1 | 1/1991 |
| EP | 0436885 A2 | 7/1991 |
| EP | 0471418 A1 | 2/1992 |
| EP | 0506420 A1 | 9/1992 |
| EP | 0515828 A1 | 12/1992 |
| EP | 0530585 A2 | 3/1993 |
| EP | 0532421 A1 | 3/1993 |
| EP | 0546460 A1 | 6/1993 |
| EP | 0649635 A1 | 4/1995 |
| EP | 0668059 A1 | 8/1995 |
| EP | 0760231 A1 | 3/1997 |
| EP | 0848600 A1 | 6/1998 |
| EP | 1132052 A2 | 9/2001 |
| EP | 1468655 A2 | 10/2004 |
| EP | 1568329 A1 | 8/2005 |
| EP | 1604619 A1 | 12/2005 |
| EP | 1658015 A1 | 5/2006 |
| EP | 1712197 A1 | 10/2006 |
| EP | 1741397 A2 | 1/2007 |
| EP | 1767160 A2 | 3/2007 |
| EP | 1878394 A2 | 1/2008 |
| EP | 2529685 | 12/2012 |
| FR | 0742618 A | 3/1933 |
| FR | 2233973 A1 | 1/1975 |
| FR | 2405062 A1 | 5/1979 |
| FR | 2405705 A1 | 5/1979 |
| FR | 2405706 A1 | 5/1979 |

(56) References Cited

FOREIGN PATENT DOCUMENTS

| | | |
|---|---|---|
| FR | 2496429 A3 | 6/1982 |
| FR | 2606268 A1 | 5/1988 |
| FR | 2622431 A1 | 5/1989 |
| FR | 2650500 A1 | 2/1991 |
| FR | 2671966 A3 | 7/1992 |
| FR | 2674118 A1 | 9/1992 |
| FR | 2677876 A1 | 12/1992 |
| FR | 2706763 A1 | 12/1994 |
| FR | 2739151 A1 | 3/1997 |
| FR | 2757370 A1 | 6/1998 |
| FR | 2802082 A1 | 6/2001 |
| GB | 0997733 A | 7/1965 |
| GB | 1237405 A | 6/1971 |
| GB | 1250413 A | 10/1971 |
| GB | 1312189 A | 4/1973 |
| GB | 1385398 A | 2/1975 |
| GB | 2017502 A | 10/1979 |
| GB | 1575194 A | 9/1980 |
| GB | 2090745 A | 7/1982 |
| GB | 2245498 A | 1/1992 |
| GB | 2257913 A | 1/1993 |
| JP | 02-121652 A | 5/1990 |
| JP | 03-058150 | 3/1991 |
| JP | 03-158150 | 7/1991 |
| JP | 04-138152 A | 5/1992 |
| JP | 06-045941 | 2/1994 |
| JP | 06-125918 | 5/1994 |
| JP | 06-245941 | 9/1994 |
| JP | 08-098846 | 4/1996 |
| JP | 08-126650 | 5/1996 |
| JP | 08-257034 | 10/1996 |
| JP | 08-266562 A | 10/1996 |
| JP | 09-108237 | 4/1997 |
| JP | 10-118096 A | 5/1998 |
| JP | 11-076259 | 3/1999 |
| JP | 11-299804 | 8/1999 |
| JP | 11-276501 | 10/1999 |
| JP | 11-512004 | 10/1999 |
| JP | 11-318930 | 11/1999 |
| JP | 2000-000247 A | 1/2000 |
| JP | 2000-152944 A | 6/2000 |
| JP | 2001-149379 A | 6/2001 |
| JP | 2001-161704 A | 6/2001 |
| JP | 2001-514039 | 9/2001 |
| JP | 2001-525701 | 12/2001 |
| JP | 2001-525702 | 12/2001 |
| JP | 2002-095673 A | 4/2002 |
| JP | 2002-232185 A | 8/2002 |
| JP | 2002-532185 A | 10/2002 |
| JP | 2002-345836 A | 12/2002 |
| JP | 2002-542875 | 12/2002 |
| JP | 2003-024344 A | 1/2003 |
| JP | 2003-038508 A | 2/2003 |
| JP | 2003-038509 A | 2/2003 |
| JP | 2003-509107 | 3/2003 |
| JP | 2003-521303 | 7/2003 |
| KR | 10-2007-0034449 A | 3/2007 |
| KR | 10-2008-0028917 A | 4/2008 |
| SU | 1037911 | 8/1983 |
| SU | 1279626 | 12/1986 |
| WO | 87/00419 A1 | 1/1987 |
| WO | 87/06982 A1 | 11/1987 |
| WO | 88/03781 A1 | 6/1988 |
| WO | 92/11819 A1 | 7/1992 |
| WO | 93/11714 A1 | 6/1993 |
| WO | 93/15678 A1 | 8/1993 |
| WO | 93/22982 A1 | 11/1993 |
| WO | 94/02073 A1 | 2/1994 |
| WO | 95/32674 A1 | 12/1995 |
| WO | 96/17556 A1 | 6/1996 |
| WO | 96/25892 A1 | 8/1996 |
| WO | 96/29948 A1 | 10/1996 |
| WO | 97/08999 A1 | 3/1997 |
| WO | 97/09000 A1 | 3/1997 |
| WO | 97/20514 A1 | 6/1997 |
| WO | 98/02105 A1 | 1/1998 |
| WO | 98/05263 A1 | 2/1998 |
| WO | 98/51226 A2 | 11/1998 |
| WO | 98/51368 A1 | 11/1998 |
| WO | 99/25266 A1 | 5/1999 |
| WO | 99/44529 A1 | 9/1999 |
| WO | 00/53110 A1 | 9/2000 |
| WO | 00/53111 A1 | 9/2000 |
| WO | 00/66012 A1 | 11/2000 |
| WO | 01/19267 A1 | 3/2001 |
| WO | 01/19268 A1 | 3/2001 |
| WO | 01/26566 | 4/2001 |
| WO | 01/54601 A1 | 8/2001 |
| WO | 01/89400 A2 | 11/2001 |
| WO | 02/71963 | 9/2002 |
| WO | 02/96309 A1 | 12/2002 |
| WO | 03/02856 | 1/2003 |
| WO | 03/22166 | 3/2003 |
| WO | 03/28567 | 4/2003 |
| WO | 03/57055 A1 | 7/2003 |
| WO | 2004/043277 A1 | 5/2004 |
| WO | 2004/089233 A1 | 10/2004 |
| WO | 2004/107957 A2 | 12/2004 |
| WO | 2005/018472 A1 | 3/2005 |
| WO | 2005/044121 A1 | 5/2005 |
| WO | 2007/014279 A2 | 2/2007 |
| WO | 2007/108734 A1 | 9/2007 |
| WO | 2009/023666 A2 | 2/2009 |
| WO | 2009/058969 A1 | 5/2009 |
| WO | 2011/032140 A1 | 3/2011 |
| WO | 2012/112327 A2 | 8/2012 |
| WO | 2013/045713 A1 | 4/2013 |
| WO | 2017/048909 A1 | 3/2017 |

OTHER PUBLICATIONS

Vattolo, M., Thesis, "The Effect of Grooves in Osteosynthesis Plates on the Restructuring of the Corticalis," Laboratory for Experimental Surgery, Swiss Research Institute, 1986 (original in German, translation to English attached with Certification).
U.S. Appl. No. 15/940,761, Locking Structures for Affixing Bone Anchors to a Bone Plate, and Related Systems and Methods, filed Mar. 29, 2018.
U.S. Appl. No. 15/926,390, Bone Plate With Form-Fitting Variable-Angle Locking Hole, filed Mar. 20, 2018.
Update, Titanium LC-DCP Condylar Buttress Plate, Jun. 15,1995 (Synthes) ("The LC-DCP update").
Universelle Rekonstruktionsplatte URP 2 4-3.2 (UniRecon-Registered), Swiss Dent, 17,1996, pp. 19-25.
The Titanium Distal Radius Plate Technique Guide, published by Synthes, 1997.
The Titanium Distal Radius Plate Technique Guide, (the "DRP Guide") published by Synthes in 1996.
The Locking Reconstruction Plate Technique Guide, published by Synthes, 1997.
The Distal Radius Plate Instrument and Implant Set Technique Guide, (Synthes) ("1999 Radius Plate Guide").
The Distal Radius Plate Instrument and Implant Set Technique Guide, (Synthes) ("1998 Radius Plate Guide").
Technique Guide: 2.4 mm Variable Angle LCP Distal Radius System. Synthes, 2008,43 pages.
Technique Guide, Less Invasive Stabilization (LISS), Oct. 2003.
Synthes' Supporting Memorandum for Reconsideration of Claim Construction (without supporting Declaration) in the Pennsylvania Action, dated Feb. 19, 2008.
Synthes' Summary Judgment Motion of No Invalidity Based on K982222 Summary including supporting memorandum, and declarations of A. Silversti and B. Liu (with supporting exhibits), dated Sep. 10, 2008.
Synthes' Responsive Claim Construction Brief (without exhibits) for the Pennsylvania Action, dated Apr. 20, 2007.
Synthes' Response to Smith & Nephew's Statement of Facts in Support of Smith & Nephew's Motion for Summary Judgment of Invalidity of the '744 patent; dated Sep. 29, 2008; 19 pages.

(56) References Cited

OTHER PUBLICATIONS

Synthes' Response to Motion for Leave to Amend Answer, Civil Action No. Mar. 0084 (E.D. Pa.), dated Aug. 9, 2007.
Synthes' Reply to Smith & Nephew's Opposition to Synthes Motion for Reconsideration of Claim Construction for the '486 patent in the Pennsylvania Action, dated Mar. 14, 2008.
Synthes' Opposition to Smith & Nephew's Motion for Summary Judgment of Invalidity of the '744 patent; dated Sep. 29, 2008; 22 pages.
Synthes' Opening Claim Construction Brief (without supporting declaration and attached exhibits but including Appendix A & B) for the Pennsylvania Action, dated Mar. 16, 2007 (Dkt. 54) (Ex. 5).
Synthes' 1996 Titanium Modular Hand System brochure (the "Hand System Brochure") [SNI-0290287-294] (Ex. 47).
Synthes Titanium Modular Hand System, 1996.
Synthes Opposition to Smith & Nephew's Motion for Summary Judgment of Invalidity of Claims 10-12 of the '486 Patent, dated Sep. 29, 2008 (Dkt. 159) (Ex 67).
Synthes 1997 Catalog, published by Synthes, Mar. 1997; part 2, 261 pgs.
Synthes 1997 Catalog, published by Synthes, Mar. 1997; part 1, 200 pgs.
Sutter, F., et al., "Titanplasma-beschichtetes Hohlschrauben—und Rekonstructions-platten-System (THRP) zur Oberbrückung van Kieferdefekten," Chirurg No. 55, pp. 741-748,1984 [SNI-0006164-171], and translation thereof [SNI-0006152-163] (Ex. 33).
Surgical Instruments Catalog, Collin & Co., 1935 (original in French, translation to English of pp. 392-397 attached with certification).
Supplemental Expert Report of Clifford FI. Turen, M.D., May 2009 (with Exhibit 1), dated Aug. 8, 2008(Ex.60).
Supplement to Apr. 9, 2008 Expert Report of John F. Witherspoon (without exhibits), dated May 14, 2008 (Ex. 74).
Supplement to Apr. 9, 2008 Expert Report of J. Lawrence Marsh in the Pennsylvania Action (with Exhibit 1), dated May 14, 2008 (Ex. 46).
Summary of Safety and Effectiveness Information [510(k) Summary], K982222, Jul. 29, 1998.
Stryker, "VariAx Distal Radius: Locking Plate System", wwvv.osteosynthesis.stryker.com, 2006, 12 pages.
Stay Order in Pennsylvania Action, dated Jul. 13, 2009.
Smith and Nephew's Opposition to Synthes Motion for Summary Judgment of No Invalidity Based on K982222(including Opposition Memorandum, Statement of Undisputed Facts, K. Doyle Declaration with Exhibits A-F and R. King's Declaration with Exhibits A-D), dated Sep. 29, 2008( Dkt. 154) (Ex. 63).
Smith & Newphew Statement of Undisputed Facts in Support of its Motion for Summary Judgment of Invalidity of U.S. Pat. No. 7,128,744; dated Sep. 29, 2008; 8 pages.
*Smith & Nephew, Inc.* v. *Rea*, Federal Circuit Opinion dated Jul. 9, 2013, 18 pages.
Smith & Nephew's Third Supplemental Response to Interrogatories Nos. 4, 5, 6, 8 and 9; Second Supplemental Responses to Interrogatories Nos. 1,2, 3,10,11 and 12; and First Supplemental Responses to Interrogatories Nos. 13,15 and 17 (with Smith & Nephew Exhibit 1 thereto), dated Aug. 11, 2008 (Ex. 14).
Smith & Nephew's Responsive Claim Construction Brief (without exhibits) for the Pennsylvania Action, dated Apr. 20, 2007 (Dkt. 60) (Ex. 8).
Smith & Nephew's Responses and Objections to Plaintiffs Fourth Set of Interrogatories Nos. 15-16, dated May 21, 2008 (Ex. 55).
Smith & Nephew's Opposition to Synthes' Motion for Reconsideration of Claim Construction for the '486 Patent in the Pennsylvania Action, dated Mar. 4, 2008 (Dkt. 108) (Ex. 11).
Smith & Nephew's Opening Claim Construction Brief (without exhibits) for the Pennsylvania Action, dated Mar. 16, 2007 (Dkt. 53) (Ex. 6).
Smith & Nephew's Memorandum in Support of Motion for Leave to file Amended Answer in the Pennsylvania Action, dated Aug. 7, 2007 (Dkt. 77) (Ex. 70).
Smith & Nephew's Memorandum in Support of its Motion for Summary Judgment of Invalidly of U.S. Pat. No. 7,128,744; dated Sep. 10, 2008; 22 pages.
Smith & Nephew's Memorandum in Support of its Motion for Partial Summary Judgment of Invalidity of Claims 10-12 of the '486 patent, dated Sep. 10, 2008.
Smith & Nephew's Amended Answer in the Pennsylvania Action (without Exhibits A-S ) in the Pennsylvania Action, dated Aug. 7, 2007.
Smith & Nephew Amended Answer and Counterclaims of Defendant, Civil Action No. 03-0084 (E.D. Pa.), dated Aug. 7, 2007.
Second Supplement to Apr. 9, 2008 Expert Report of J. Lawrence Marsh (with Exhibit 1), dated Sep. 3, 2008.
Second Supplement to Apr. 9, 2008 Expert Report of David Seligson, M.D., dated Sep. 3, 2008.
Schuhli Technique Guide, published by Synthes, 1995.
Schuhli Technique Guide 1998, (Synthes) ("Schuhli Guide").
Schmoker, The Locking Reconstruction Plate 2.4-3.2, originally published in Swiss Dent 17,1996.
Schandelmaier, et al., Distal Femur Fractures and LISS Stabilization, Injury, Int. J. Care Injured, vol. 32, Suppl. 3, 55-63, 2001.
Ring, D., et al. "Prospective Multicenter Trial of a Plate for Distal Fixation of Distal Radius Fractures," J. of Hand Surgery, vol. 22a(5), pp. 777-784, Sep. 1997.
Ring, D., et al,"A New Plate for Internal Fixation of the Distal Radius," AO.ASIF Dialogue, vol. IX, issue I, Jun. 1996 [SNI-0254971-973] (Ex. 53).
Reply to Counterclaims, Civil Action No. 03-0084 (E.D. Pa.), filed Jan. 2, 2007.
Rebuttal Expert Report of Russell Parsons, Ph.D., (with Exhibit 1), dated Jul. 15, 2008.
Rebuttal Expert Report of Mad Truman, P.E., (with Exhibit 2), dated May 14, 2008 (Ex. 79).
Rebuttal Expert Report of Eric R. Gozna, M.D., P.ENG., (with Exhibit 1), dated May 13, 2008 (Ex. 56).
Rebuttal Expert Report of Clifford H. Turen, M.D., (with Exhibit 1 ), dated May 14, 2008.
Rebuttal Expert Report of Charles E. Van Horn (without Exhibits), dated May 12, 2008 (Ex. 77).
Pure Titanium Implants Catalog, published Dec. 1993 (Synthes) ("PTI") [SN10259670-673] (Ex. 23).
Printout of http://www.aofoundation.org web site, dated May 23, 2007 (attached as Exhibit L to Amended Answer).
Printout from USFDA 510(k) Premarket Notification Database, dated May 23, 2007, listing Synthes Distal Femur Plate (DFP) System, and bearing 510(k) No. K982222 (attached as Exhibit N to Amended Answer.
Printout from USFDA 510(k) Premarket Notification Database, dated May 22, 2007, listing Synthes 2.4 mm Universal Locking Plate System, and bearing 510(k) No. K961421 (attached as Exhibit R to Amended Answer).
Printout from US FDA 510(k) Premarket Notification Database, dated May 22, 2007, listing Synthes Anatomical Locking Plate System, and bearing 510(k) No. K961413 (attached as Exhibit P to Amended Answer).
Photographs of the Bolhofner Distal Femur Plating System (Bolhofner DFPS), Apr. 14, 2008.
Perren, S., et al., "Early Temporary Porosis of Bone Induced by Internal Fixation Implants," Clinical Orthopaedics and Related Research, No. 232, Jul. 1988, 139-151.
Perren, et al., "The Limited Contact Dynamic Compression Plate (LC-DCP)," Arch. Orthopaedic & Trauma Surg., 1990, vol. 109, 304-310.
Ms. Truman's Jul. 24, 2008 deposition transcript in the Pennsylvania Action (Ex. 81).
Mr. Van Horn's Jul. 15, 2008 deposition transcript in the Pennsylvania Action (Ex. 78).
Marsh Exhibit C, Declaration of J. Lawrence Marsh, MD., in support of Smith & Nephew's, Inc's Motion for Partial Summary Judgement of Invalidity of Claims 10-12 of U.S. Pat. No. 6,623,486, dated Sep. 9, 2008, pp. 1-20.

(56) References Cited

OTHER PUBLICATIONS

Marsh Exhibit B, Supplement to Apr. 9, 2008 Expert Report of J. Lawrence Marsh, MD, Civil Action No. 03-0084, dated May 14, 2008 , pp. 1-19.
Marsh Exhibit A, Releasable 510(k) Search, Aug. 7, 2000, http://web.archive.org/web/19970615015534/www.fda.gov/egibin/htmlscript? 510k.hts+showcat-OR.
Marsh Exhibit A, Initial Expert Report of J. Lawrence Marsh, MD, Civil Action No. 03-0084, dated Apr. 9, 2008 , pp. 1-181.
Marsh Exhibit 1, Curriculum Vitae, Dec. 2006, pp. 1-34.
Marsh Exhibit 1, Affidavit of Christopher Butler dated Aug. 24, 2010.
Manual of Internal Fixation, Techniques Recommended by the AO-ASIG Group, Springer-Verlag, 1991,200-251.
Luthi, U., etal., "Kontackflache zwischen Osteosyntheseplatte and Knochen," Aktuel. Traumatol. 10:131-136,1980 ("Luthi") [SNI-0258572-577] (Ex. 31).
Less Invasive Stabilization System LISS Surgical Technique Proximal Tibia, (Draft), 2000,11 pgs.
Krettek et al.; "Distale Femurfrakturen"; Swiss Surg.; 1998; 4; p. 263-278 with English abstract.
Krettek et al, "LISS less Invasive Stabilization System," AO International Dialogue, vol. 12, Issue I, Jun. 1999.
Koval, k., et al., "Distal Femoral Fixation: A Biomechanical Comparison of the Standard Condylar Buttress Plate, a Locked Buttress Plate, and the 95-Degree Blade Plate," J. of Orthopaedic Trauma, val. 11(7), pp. 521-524, Lippencott-Raven Publishers, Oct. 1997.
Kolodziej, P., et al. "Biomechanical Evaluation of the Schuhli Nut," Clinical Orthopaedics and Related Research, No. 34 7, pp. 79-85, Lippencott-Raven Publishers, Feb. 1988 ("Kolodziej") [SNI-0256042-048] (Ex. 28).
Kassab, et al., "Patients Treated for Nonunions with Plate and Screw Fixation and Adjunctive Locking Nuts," Clinical Orthopaedics and Related Research, 1998, 347, 86-92.
Joint submission selling forth agreed claim construction in the Pennsylvania Action, dated Jul. 31, 2007.
International Search Report for International Application No. PCT/CH03/00577, dated Apr. 28, 2004, English language translation of the German language version.
International Patent Application No. PCT/US2008/072894: International Search Report dated Mar. 19, 2009, 18 pages.
Initial Expert Report of J. Lawrence Marsh, M.D., Apr. 9, 2008 (with Exhibits 1-2 and Appendices A-L), dated Apr. 9, 2008 (Ex. 41).
Initial Disclosures of Defendant, Civil Action No. 03-0084 (E.D. Pa), dated Jan. 12, 2007.
Information Disclosure Statement in U.S. Appl. No. 09/660,287, dated Nov. 13, 2000 (attached as Exhibit G to Amended Answer).
Information Disclosure Statement bearing, dated May 4, 2001 (attached as Exhibit F to Amended Answer).
Haas, N.P., et al., "LISS-Less Invasive Stabilization System—A New Internal Fixator for Distal Femur Fractures," OP J., vol. 13(3), pp. 340-344, Georg Thieme Verlag, Dec. 1997 (in English).
Gautier, E., et al., "Porosity and Remodelling of Plated Bone After Internal Fixation: Result of Stress Shielding of Vascular Damage?", Biomaterials and Biomechanics 1983, Elsevier Science Publishers B.V. 1984 ("Gautier").
Expert Report of John F. Witherspoon (w/o Exhibits A-C) in the Pennsylvania Action, dated Apr. 9, 2008; 36 pages.
European Patent Application No. 12006617: Extended European Search Report dated Jan. 21, 2013, 8 pages.
European Patent Application No. 12006615.4: Extended European Search Report dated Jan. 21, 2013, 7 pages.
European Patent Application No. 12006606.3: Extended European Search Report dated Jan. 21, 2013, 7 pages.
English translation of International Patent Application No. PCT/CH03/00577: International Search Report dated Apr. 28, 2004, 6 pages.
English translation of International Patent Application No. PCT/CH03/00577: International Search Report dated Apr. 28, 2004, 4 pages.
Dr. Turen's Aug. 15, 2008 deposition transcript in the Pennsylvania Action (Ex. 61).
Dr. Parsons Aug. 7, 2008 deposition transcript in the Pennsylvania Action (Ex. 58).
Dr. Marsh's Jul. 26, 2008 Deposition transcript in the Pennsylvania Action (Ex. 52).
Docket sheet for the Pennsylvania Action—2:03-cv-0084 (CDJ) (Ex. 4) filed Jan. 7, 2003.
Docket sheet for the California Action—3:07-cv-00309-L-AJB (Ex. 1) Filed Feb. 14, 2007.
Defendant's Motion for Leave to Amend Answer to Assert Allegations of Inequitable Conduct, Civil Action No. 03-0084 (E.D. Pa.), dated Aug. 7, 2007.
Declaration of Robert A. King in Support of their Motion for Partial Summary Judgment of Invalidity of Claims 10-12 of U.S. Pat. No. 6,623,486 (without exhibits), dated Sep. 10, 2008.
Declaration of J. Russell Parsons, Ph.D. in Support of Synthes Opposition to Smith & Nephew's Motion for Summary Judgement of Invalidity of the '744 patent (w/o Exhibits 1-4) dated Sep. 29, 2008; 15 pages.
Declaration of J. Russell Parsons, Ph.D. in Support of Synthes Opposition to Smith & Nephew's Motion for Partial Summary Judgment of Invalidity of Method Claims 10-12 of U.S. Pat. No. 6,623,486 (with Exhibits 1-4), dated Sep. 29, 2008 (Dkt. 160) (Ex. 68).
Declaration of J. Lawrence Marsh, M.D. dated Nov. 22, 2010.
Declaration of J. Lawrence Marsh, M.D. dated Jun. 25, 2010.
Declaration of J. Lawrence Marsh, M.D. dated Jun. 3, 2010.
Declaration of Dr. Seligson in Support of Smith & Nephew's Motion for Partial Summary 175 Judgment of Invalidity of Claims 10-12 of U.S. Pat. No. 6,623,486 dated Sep. 9, 2008 (with Exhibit 1, pp. 16-66 dated Sep. 10, 2008).
Declaration of Clifford H. Turen, M.D. in Support of Synthes' Opposition to Smith & Nephew's Motion for Partial Summary Judgment of Invalidity of Method Claims 10-12 of U.S. Pat. No. 6,623,486 (with Exhibits 1-4 ), dated Sep. 29, 2008.
Declaration of Charles E. Van Horn, Esq., in Support of Synthes Opposition to Smith & Nephew's Motion for Summary Judgement of Invalidity of the '744 patent (w/o Exhibits 1-6) dated Sep. 29, 2008; 12 pages.
Court Order denying Synthes' Motion for Reconsideration of Claim Construction for the '486 Patent in the Pennsylvania Action, dated Jun. 30, 2008.
Collins Instruments de Chirurgie, published 1935, as illustrated at http://www.litos.com/pages/winkelstabilitaet e.html (Sep. 26, 2007) ("Collin Catalog") [SNI-0258552-556] (Ex. 20).
Claim Construction Order in Pennsylvania Action, dated Feb. 4, 2008.
Brief in Support of Defendants' Motion for Leave to Amend Answer to Assert Allegations of Inequitable Conduct, Civil Action No. 03-0084 (E.D. Pa.), dated Aug. 7, 2007.
Bolhofner, et al., The Results of Open Reduction and Internal Fixation of Distal Femur Fractures Using a Biologic (Indirect) Reduction Technique; Journal of Orthopedic Trauma, vol. 10, No. 6, pp. 372-377, Liooincort-Raven Publishers, Copyright 1996.
AO/ASIF Instruments and Implants, A Technical Manual, Springer-Verlag, 1994 (the "AO-ASIF Manual").
Answer to Amended Complaint and Counterclaims, Civil Action No. 03-0084 (E . . . D. Pa), filed Dec. 5, 2006.
Amended Complaint for Patent Infringement, Civil Action No. 03-0084 (E.D. Pa.), filed Nov. 13, 2006.
ACE SymmetryTM, "Curves in All the Right Places", 1996, 3 pages.
ACE Symmetry, "Curves in All the Right Places", 1996, 3 pages.
ACE Symmetry Trademark Titanium Upper Extremity Plates, ACE Medical Company, 1996, 2 pages.
ACE Symmetry (Trademark), "Curves in All the Right Places", Titanium Upper Extremity Plates, Ace Medical Company, 1996, 6 pages.

(56) References Cited

OTHER PUBLICATIONS

510(k) Summary for Synthes (USA)'s Distal Femur Plate (DFP) System (K982222), dated Jul. 29, 1998 (attached as Exhibit O to Amended Answer).
510(k) Summary for Synthes (USA)'s Anatomical Locking Plate System (K961413), dated Aug. 7, 1996 (attached as Exhibit Q to Amended Answer).
510(k) Summary for Synthes (USA)'s 2.4 mm Universal Locking Plate System (K961421 ), dated Jun. 26, 1996 (attached as Exhibit S to Amended Answer).
510(k) Disclosure K982732, Oct. 8, 1998 (Synthes) ("K982732") [SNI-0259741-744] (Ex. 39).
510(k) Disclosure K963798, Nov. 27, 1996 (Synthes) ("K963798") [SNI-0258398] (Ex. 38).
510(k) Disclosure K962616, Sep. 3, 1996 (Synthes) ("K962616") [SNI-0258397] (Ex. 37).
510(k) Disclosure K961421, Jun. 26, 1996 (Synthes) ("K961421 ") [SNI-0258396] (Ex. 36).
510(k) Disclosure K961413, Aug. 7, 1996 (Synthes) ("K961413") [SNI-0259751] (Ex. 35).
4.5 mm Cannulated Screw Technique Guide, published 1995 (Synthes) [SNI-0259703-714] (Ex. 21).
35 U.S.C. .sctn.282 Notice in the Pennsylvania Action, dated Oct. 10, 2008 (Ex. 40).
35 U.S.C. .sctn.282 Notice in the Pennsylvania Action, dated Oct. 10, 2008.
"VariAx TM Distal Radius Locking Plate System", Stryker R, Copyright 2009,12 pages.
"The New Comprehensive Stryker R VariAx TM Distal Radius Locking Plate System", Copyright 2009,20 pages.
"Multiple Offerings of Plates, Screws and Pegs", Small Bone Innovations, Inc., Dec. 2009, 2 pages.
"less Invasive Stabilization System (LISS) Technique Guide," Synthes (USA) Copyright 2000 (attached as Exhibit K to Amended Answer).
"Cone Drive History and Double Enveloping Technology", http://conedrive.com/history/html., accessed Apr. 20, 2006, 9 pages.

* cited by examiner

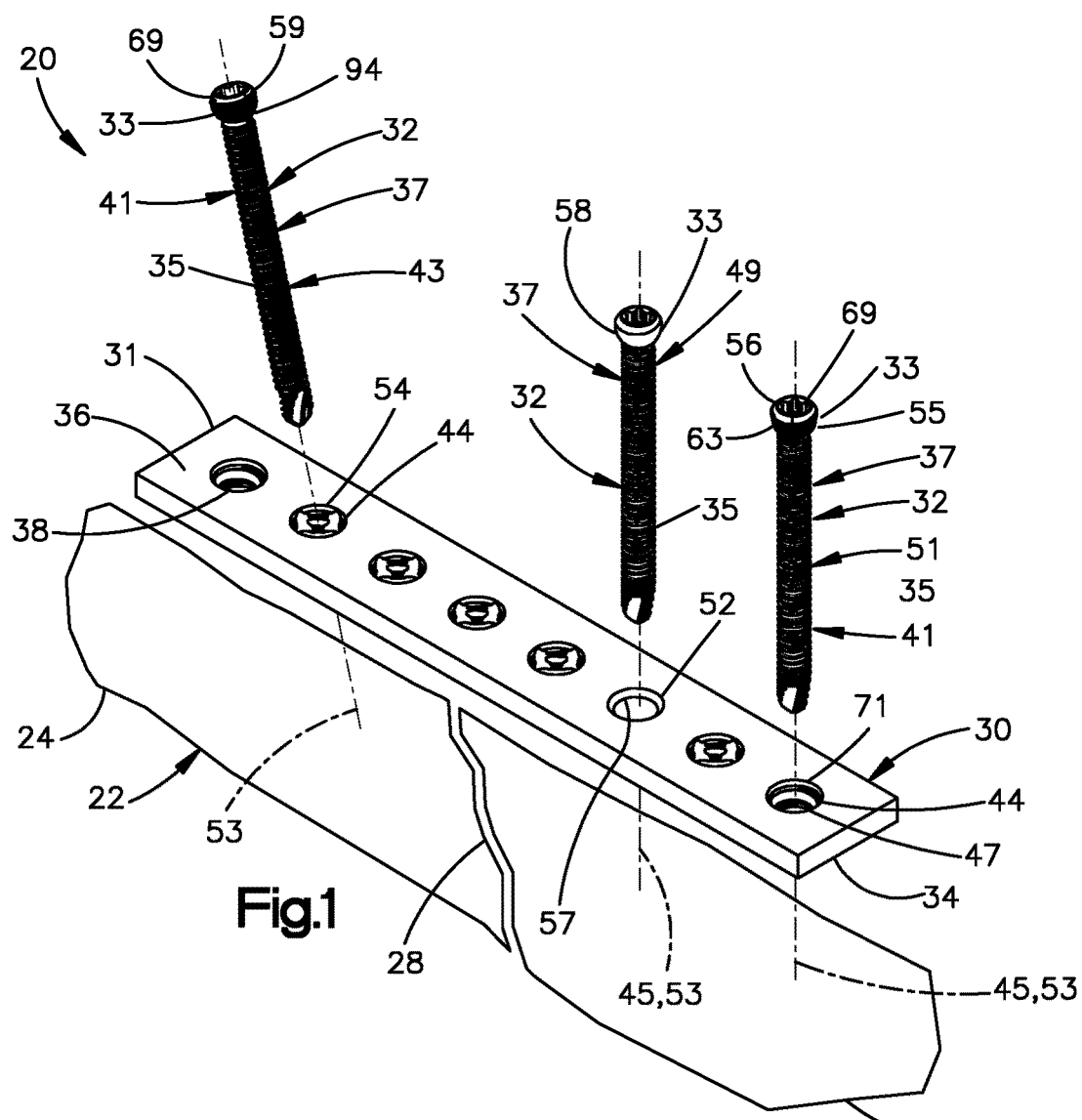
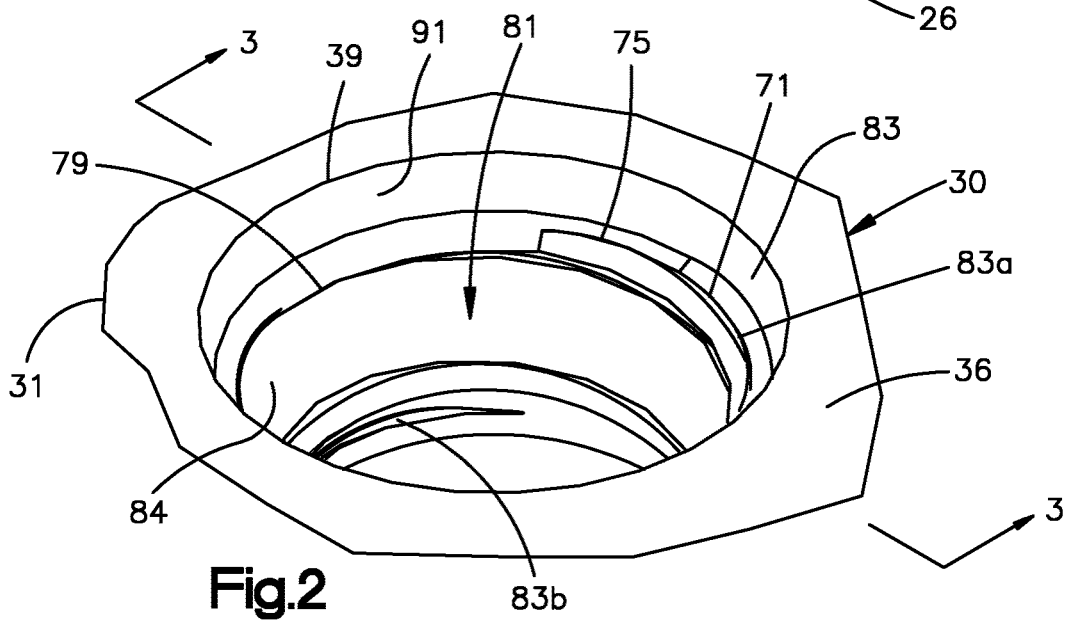

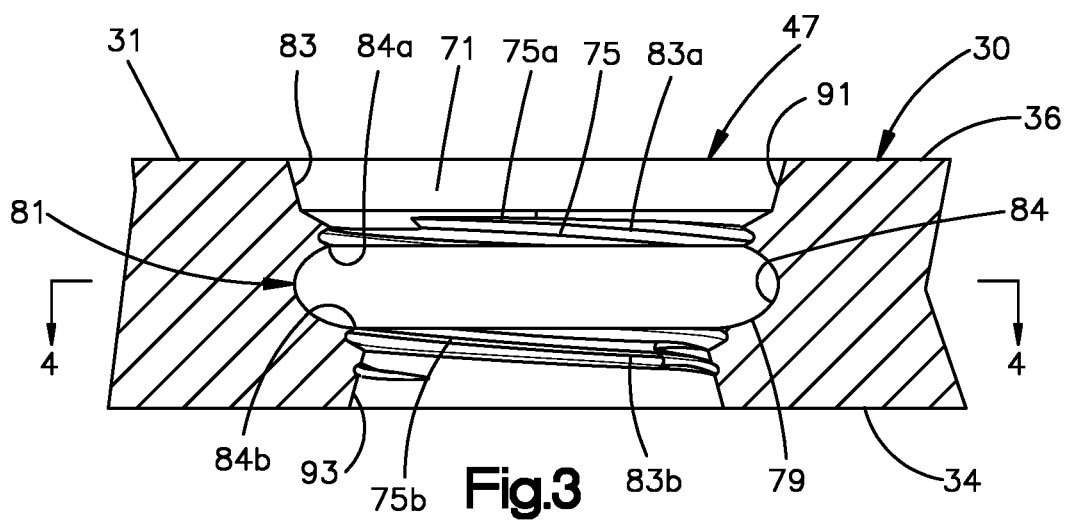
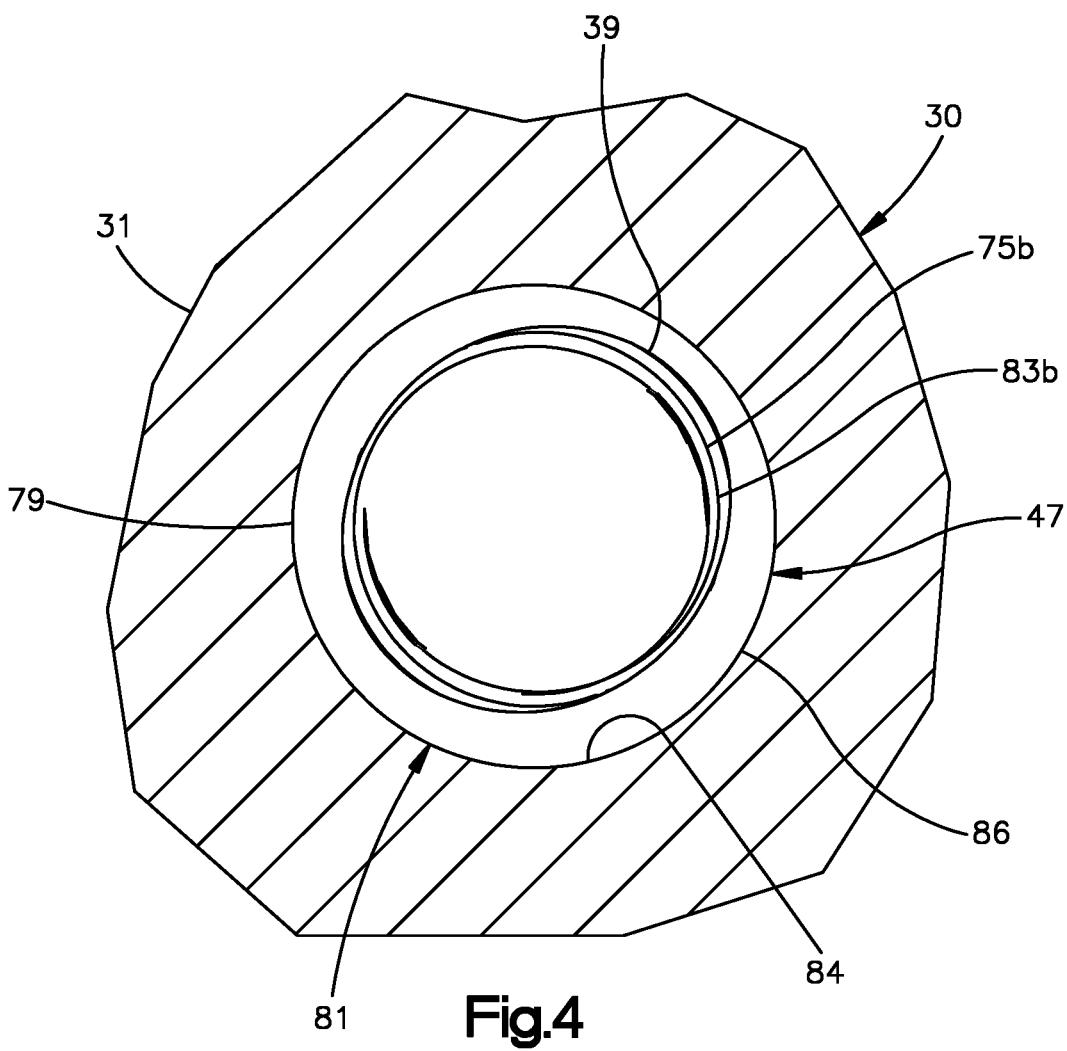

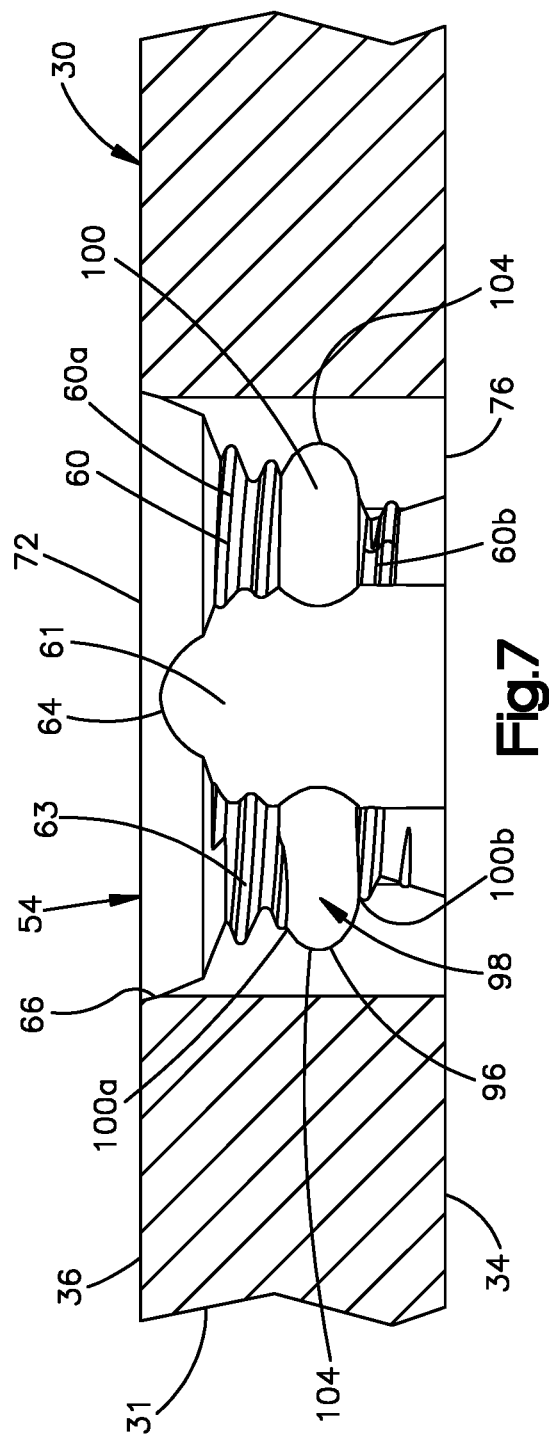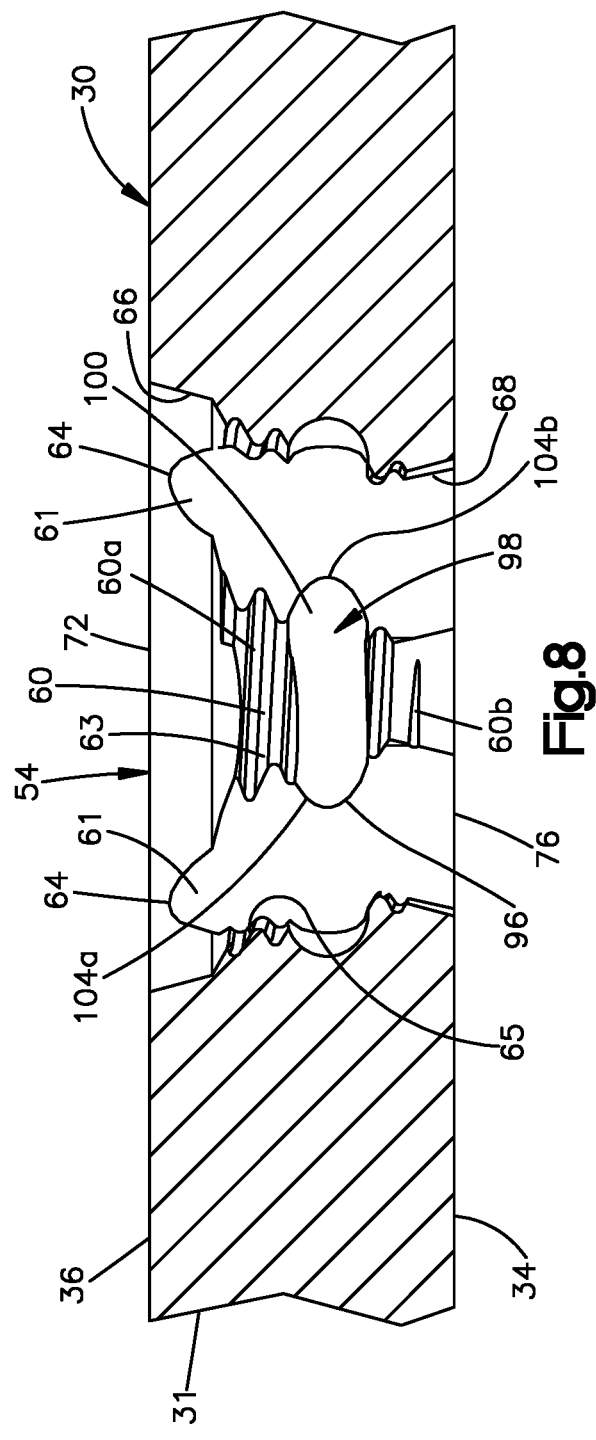

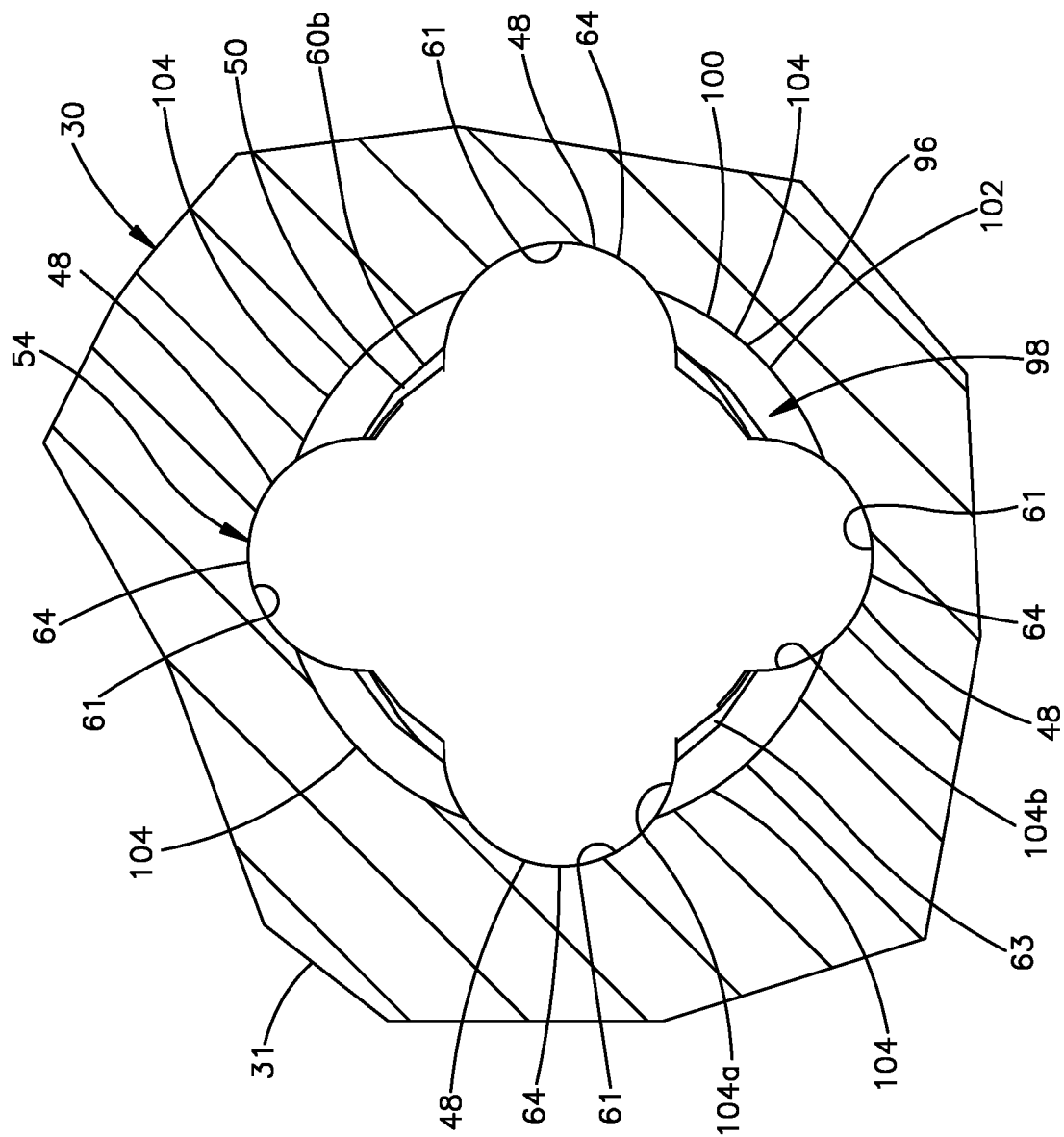

IMPLANT HAVING LOCKING HOLES WITH COLLECTION CAVITY FOR SHAVINGS

BACKGROUND

When bones are damaged through trauma, disease, distraction osteogenesis, or orthognathic surgery, the defect is typically reduced, and bone fixation plates are commonly applied to the bone on sides of the defect to ensure union in the desired position. Bone screws can be sized to be driven through respective fixation holes of the plate and into the underlying bone to secure the bone plate to the bone. One common bone screw used in such applications is generally referred to as a locking screw that mate with threaded locking fixation holes of the bone plate. Locking screws have threaded heads that purchase with the threads in the locking fixation holes of the plate to reach a stable construct that prevents loosening or backing out of the screws. In particular, the locking screw can be driven through the plate fixation hole and into the underlying bone until the head threadedly mates with the bone plate in the locking fixation hole. The threaded heads of locking screws typically do not apply a compressive force against the bone plate toward the underlying bone.

One consideration when designing locking screws and locking fixation holes is the prevention the threads of the screw head from cross-threading with the threads in the locking fixation hole of the bone plate. Such cross-threading is associated with the production of shavings from the screw head, the bone plate, or both.

SUMMARY

According to one example of the present disclosure, a bone plate is configured to receive a locking bone screw. The bone plate defines an inner surface configured to face the underlying bone, and an outer surface opposite the inner surface along an axial direction. The bone plate can include a threaded internal locking surface that extends between the outer surface and the inner surface so as to define a locking hole that is oriented along a central hole axis. The internal locking surface can define a collection cavity disposed between the outer surface and the inner surface. The collection cavity can be configured to collect a shaving that is produced from one of the bone plate and the locking bone screw while the locking bone screw is threadedly mated with the bone plate.

BRIEF DESCRIPTION OF THE DRAWINGS

The foregoing summary, as well as the following detailed description of illustrative embodiments of the present application, will be better understood when read in conjunction with the appended drawings. For the purposes of illustrating the locking structures of the present application, there is shown in the drawings illustrative embodiments. It should be understood, however, that the application is not limited to the precise arrangements and instrumentalities shown. In the drawings:

FIG. 1 is an exploded perspective view of a bone fixation system including a bone plate and a plurality of bone screws configured to be fixed to an underlying bone;

FIG. 2 is an enlarged perspective view of a portion of the bone plate illustrated in FIG. 1, showing a standard-type locking hole;

FIG. 3 is a sectional side elevation view of the portion of the bone plate illustrated in FIG. 2, taken along line 3-3;

FIG. 4 is a sectional plan view of the portion of the bone plate illustrated in FIG. 3, taken along line 4-4;

FIG. 7 is a to plan view of the portion of the bone plate illustrated in FIG. 7;

FIG. 8 is a sectional side elevation view of the portion of the bone plate illustrated in FIG. 7, taken along line 8-8;

FIG. 9 is another sectional side elevation view of the portion of the bone plate illustrated in FIG. 7, taken along line 9-9.

DETAILED DESCRIPTION

Figure 5:
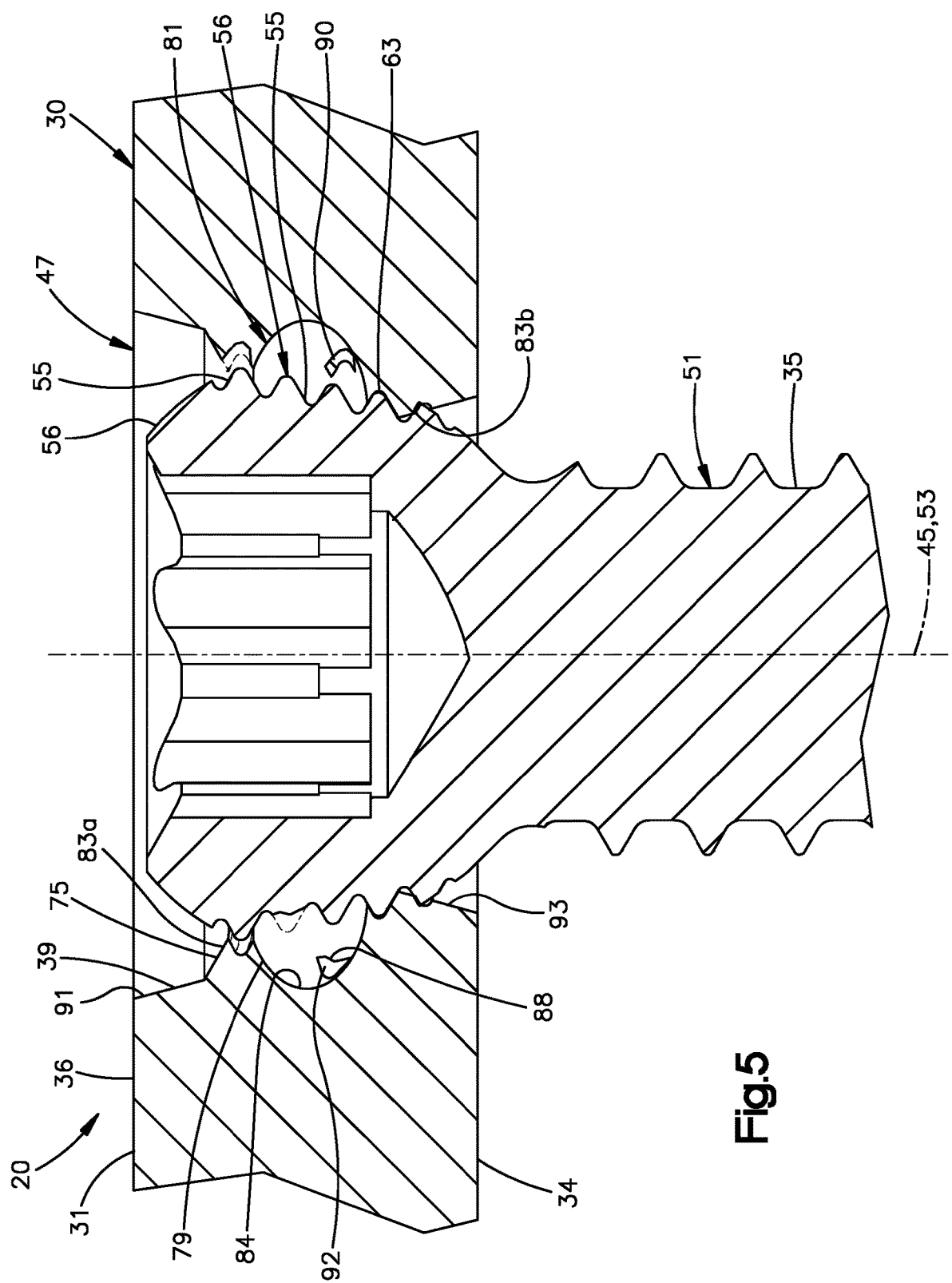
FIG. 5 is a sectional side elevation view of the portion of the bone plate illustrated in FIG. 2, shown with the bone screw illustrated in FIG. 1 being driven into the hole and producing shavings.
Figure 6:
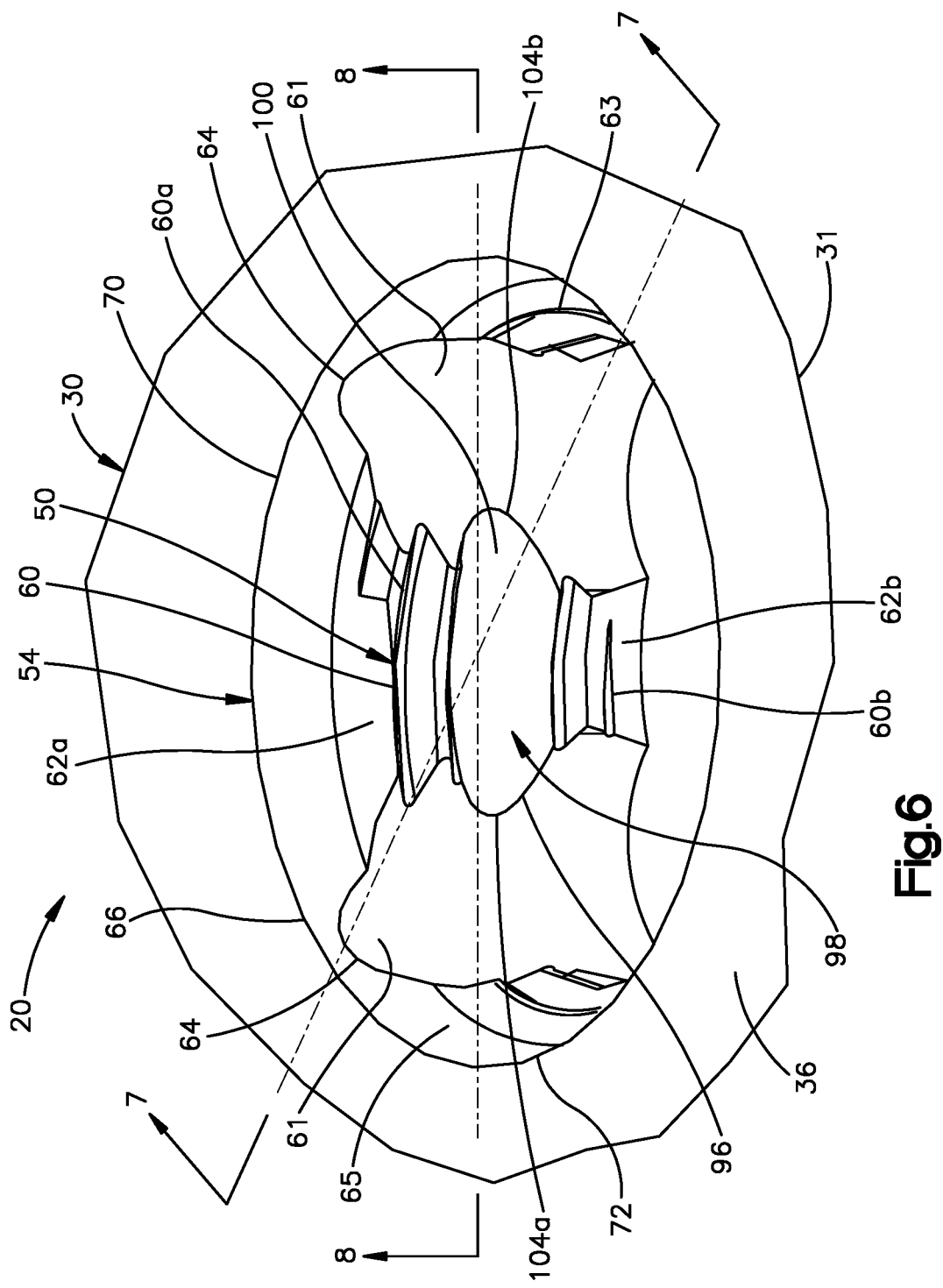
FIG. 6 is an enlarged perspective view of a portion of the bone plate illustrated in FIG. 1, showing a variable-angle locking hole.

The present disclosure can be understood more readily by reference to the following detailed description taken in connection with the accompanying figures and examples, which form a part of this disclosure. It is to be understood that this disclosure is not limited to the specific devices, methods, applications, conditions or parameters described and/or shown herein, and that the terminology used herein is for the purpose of describing particular embodiments by way of example only and is not intended to be limiting of the scope of the present disclosure. Also, as used in the specification including the appended claims, the singular forms "a," "an," and "the" include the plural, and reference to a particular numerical value includes at least that particular value, unless the context clearly dictates otherwise.

The term "plurality", as used herein, means more than one. When a range of values is expressed, another embodiment includes from the one particular value and/or to the other particular value. Similarly, when values are expressed as approximations, by use of the antecedent "about," it will be understood that the particular value forms another embodiment. All ranges are inclusive and combinable.

Referring initially to FIG. 1, a bone fixation system 20 is configured to be implanted onto bone 22 so as to stabilize a first bone segment 24 with respect to a second bone segment 26 that is separated from the first bone segment 24 by a defect 28. In one example, the first bone segment 24 can be defined by the diaphysis of the bone, while the second bone segment 26 can be defined by the epiphysis of the bone. It should be appreciated, however, that the first and second bone segments 24 and 26 can be defined by any region of the bone 22 as desired. Further, the bone 22 can be any bone in the human or animal anatomy suitable for bone plate fixation. Further still, while the bone 22 is illustrated having first and second bone segments 24 and 26, it is appreciated that the bone 22 can include any number of defects or bone fragments as desired that are configured for fixation using the bone fixation system 20. For instance, the diaphysis of the bone can include a plurality of bone fragments.

The bone fixation system 20 can include a bone plate 30 and a plurality of bone anchors 32 that are configured to fix the bone plate 30 to the underlying bone 22, and in particular to each of the first and second bone segments 24 and 26. The bone anchors 32 include a head 33 and a shaft 35 that extends out with respect to the head 33 along a respective central axis 53. The shaft 35 can extend directly from the head 33, or can extend from a neck that is disposed between the head 33 and the shaft 35. The shaft 35 can be threaded, such that the bone anchor 32 is configured as a bone screw 37 whose shaft 35 extends out relative to the head 33 along the central axis 53, which can also be referred to as a central screw axis 53.

The threaded shaft 35 can be configured to threadedly purchase in the underlying bone 22. For instance, one or more up to all of the bone screw 37 can be configured as a cortical screw whose threaded shaft 35 is designed and configured to threadedly mate to cortical bone. Alternatively or additionally, one or more of the bone screws 37 can be configured as a cancellous screw whose threaded shaft 35 is designed and configured to threadedly mate to cancellous bone. It is appreciated that cancellous bone screws typically have threads that have a greater pitch than threads of cortical bone screws. Further, the threads of cancellous bone screws typically extend out from the shaft of the bone screw a greater distance than the threads of cortical bone screws.

The bone plate 30 defines a bone plate body 31. The bone plate body 31, and thus the bone plate 30, defines a bone-facing inner surface 34 configured to face the underlying bone 22, and an outer surface 36 that is opposite the inner surface 34 along a transverse direction T. The bone plate 30 further defines a plurality of fixation holes 38 that extend through the bone plate body 31 from the inner surface 34 to the outer surface 36. In particular, each of the fixation holes 38 extends through the bone plate body 31, and thus through the bone plate 30, along a respective central hole axis 45. The central hole axis 45 is oriented along an axial direction. The axial direction can be coincident with the transverse direction T. Thus, the central hole axis 45 can be oriented normal to each of the inner surface 34 and the outer surface 36. It should be appreciated, of course, that the axial direction defined by the central hole axis 45 can be oriented in any suitable direction as desired, including a direction oblique to the transverse direction T.

The fixation holes 38 are each sized to receive the shaft 35 of a respective one of the bone screws 37. The bone screws 37 that extend through fixation holes 38 are permanent bone screws, meaning that they remain after completion of the surgical procedure. This is distinguished from temporary fixation holes that, for instance, can be configured to receive temporary fixation members, such as Kirschner wires that are removed prior to completion of the surgical procedure. In this regard, the fixation holes 38 can be referred to as permanent fixation holes. Accordingly, during operation, the shaft 35 of the bone screw 37 can be inserted through a respective one of the fixation holes 38 and into the underlying bone 22. The bone screw 37 can then be rotated so as to cause the threaded shaft 35 to be driven into the underlying bone 22 as the threaded shaft 35 threadedly purchases with the underlying bone. The threaded shaft 35 can be driven into the underlying bone 22 until the head 33 engages the bone plate 30. The heads 33 of the bone screws 37 can engage the bone plate 30 in various different manners as will now be described.

For instance, certain ones of the fixation holes 38 can be unthreaded compression fixation holes 52, while certain others of the fixation holes 38 can be threaded locking holes 44. Still other ones of the fixation holes 38 can be a combination hole, whereby a threaded locking hole 44 and an unthreaded compression hole 52 intersect each other to define a combination hole.

Thus, one or more of the bone screws 37 can be configured as a compression screw 49 whose head 33 defines a compression head 58 that is configured to bear against the bone plate 30 in the compression hole 52 so as to apply a compressive force against the bone plate 30 toward the underlying bone 22. In particular, the bone plate 30 can define an internal compression surface 57 that can extend between the outer surface 36 and the inner surface 34 so as to at least partially define the compression hole 52. During operation, the shaft 35 of the compression screw 49 can be inserted through the compression hole 52 and driven into the underlying bone 22 as described above. In particular, rotation of the bone screw 37 causes the compression head 58 to compress against the internal compression surface 57. As a result, the compression head 58 causes the bone plate 30 to apply a compressive force against the underlying bone. At least a portion of the internal compression surface 57 is typically spherical or otherwise tapered with respect to the central hole axis 45 as it extends in an axially inward direction from the outer surface 36 toward the inner surface 34. The taper of the internal compression surface 57 prevents the compression head 58 from passing completely through the compression hole 52. The compression head 58 typically has an unthreaded external surface. Similarly, at least a portion up to an entirety of the internal compression surface 57 that abuts the unthreaded external surface of the compression head 58 is typically unthreaded. Thus, it is common to drive compression screws 49 into the unthreaded compression holes 52.

With continuing reference to FIG. 1, the bone plate 30 can alternatively or additionally define at least one or more threaded locking holes 44 that are each configured to threadedly purchase with a respective one of the bone screws 37. For instance, the bone plate 30 can define a plurality of threaded internal locking surfaces 65 that can extend from the bone-facing inner surface 34 to the outer surface 36. Thus, the threaded internal locking surfaces 65 can at least partially define respective ones of the locking holes 44.

Thus, at least one or more of the bone screws 37 can be configured as locking screws 41 that are configured to threadedly purchase with the bone plate 30 inside the threaded locking holes 44. In particular, the locking screws 41 can include an externally threaded locking screw head 69 that is configured to threadedly mate with a respective one of the threaded internal surfaces 65 of the bone plate 30 inside the respective locking hole 44. During operation, the shaft 35 of the locking screw 41 can be inserted through the fixation hole 38 and driven into the underlying bone 22 as described above. In particular, rotation of the screw 37 causes the threaded head 69 to threadedly mate with the threaded locking hole 44. As a result, the threaded screw head 69 fastens the bone plate 30 to the underlying bone 22 without applying a compressive force onto the bone plate 30 against the underlying bone 22. The bone plate 30 can be spaced from the underlying bone 22 when the threaded head 69 is threadedly mated with the threaded internal surface 65. Alternatively, the bone plate 30 can abut the underlying bone 22 when the threaded head 69 is threadedly mated with the threaded internal surface 65. At least a portion of the threaded internal surface 65 is typically tapered with respect to the central hole axis 45 as it extends in the axially inward direction from the outer surface 36 toward the inner surface 34. The taper of the threaded internal surface 65 is configured to prevent the threaded head 69 from passing completely through the threaded locking hole 44. Because the bone plate 30 can include both compression fixation holes 52 and threaded locking holes 44, the bone plate 30 can be referred to as a locking compression plate.

Alternatively or additionally, one more of the locking screws 41 can be configured as a standard-type locking bone screw 51. The externally threaded head 69 of the standard-type locking bone screw 51 can be configured as a standard-type threaded locking head 56. In particular, the standard-type threaded locking head 56 defines an external surface 55 and at least one helical thread 63 that extends from the external surface 55. The external surface 55 can be conically tapered or alternatively shaped as desired. The at least one thread 63 can be configured as a single lead thread, a double lead thread, or any number of leads as desired. The thread 63 extends greater than one full revolution about the central screw axis 53 so as to be configured to threadedly purchase with the standard-type locking head 56. Correspondingly, one or more of the threaded locking holes 44 can be configured as standard-type locking hole 47. In particular, the standard-type locking head 56 is configured to threadedly mate with the bone plate 30 in the standard-type locking hole 47 when the central screw axis 53 of the standard-type locking bone screw 51 is oriented at a predetermined orientation with respect to the central hole axis 45. For instance, the standard-type locking head 56 is configured to threadedly mate with the threaded internal surface 65 in the standard-type locking hole 47.

The predetermined orientation can be a nominal orientation whereby the central screw axis 53 is coincident with the central hole axis 45. Alternatively, the predetermined orientation can be defined when the central screw axis 53 is oriented oblique to the central hole axis 45. In certain examples, the standard-type locking screw 51 is configured to threadedly mate with the bone plate 30 in the standard-type locking hole 47 only when the bone screw 51 is oriented at the predetermined orientation. In one example, at least one or more up to all of the fixation holes 38 in the plate head portion can be configured as standard-type locking holes 47.

Alternatively or additionally, one more of the locking screws 41 can be configured as a variable angle (VA) locking bone screw 43. The externally threaded head 69 of the VA locking screw 43 can be configured as a VA threaded locking head 59. Correspondingly, one or more of the threaded locking holes 44 can be configured as variable angle (VA) locking holes 54. In particular, the VA threaded head 59 is configured to threadedly mate with the bone plate 30 in the VA locking holes 54 when the central screw axis 53 of the VA bone screw 43 is oriented at any one of a plurality of angles within a range of angles with respect to the central hole axis 45 at which the VA threaded head 59 is configured to threadedly mate with the bone plate 30 in the VA locking hole 54. For instance, the VA locking head 59 is configured to threadedly mate with the threaded internal surface 65 in the VA locking hole 54. In one example, at least one or more up to all of the fixation holes 38 in the plate head portion can be configured as VA locking holes 54.

The bone plate 30 and the locking screws 41 can each comprise one or more biocompatible materials, such as titanium, titanium alloys (e.g., titanium-aluminum-niobium (TAN) alloys, such as Ti-6Al-7Nb), stainless steel, cobalt base alloys, composite materials, and polymeric materials and/or ceramic materials, by way of non-limiting examples. In one example, the material of the locking screws 41 can have a hardness that is greater than that of the bone plate 30. For instance, the bone plate 30 can primarily or entirely be made of titanium, and the locking screws 41 can primarily or entirely comprise Ti-6Al-7Nb (TAN). Alternatively, the hardness of the bone plate 30 can be greater than that of the locking screws 41. Alternatively, the hardness of the bone plate 30 can be equal to that of the locking screws 41.

While the bone plate 30 has been described in accordance with one specific example, it should be appreciated that the bone plate 30 can be configured in any suitable manner as desired. Further, bone plates 30 constructed in accordance with any of the examples described herein can be configured to attach to any region or region or regions of any suitable bone in the human or animal anatomy suitable for bone plate fixation.

The present inventors recognize that misalignment of the threaded locking heads 69 of locking screws 41 with the internal locking surface 65 can result in cross-threading between the threaded locking heads 69 and the internal locking surface 65. Cross-threading can occur when the threads of the threaded locking heads 69 of the locking screw do not fit appropriately with the threads of the internal locking surface 65 within the locking holes 44. Cross-threading is problematic because it can reduce the interference fit (also referred to as the "form-fit") between the threads of the locking heads 69 with the threads of the internal locking surface 65, which can result in the production of shavings as the locking head 69 is threadedly mated with the internal locking surface 65.

For instance, when the threaded locking head 69 is harder than the internal locking surface 65, cross-threading can cause the locking screw 41, and in particular the threaded locking heads 69, to shave material from the bone plate 30, and in particular the internal locking surface 65, thereby creating shavings of the bone plate 30, and in particular of the internal locking surface 65. Alternatively, when the internal locking surface 65 is harder than the threaded locking head 69, cross-threading can cause the bone plate 30, and in particular the internal locking surface 65, to shave material from the locking screw 41, and in particular the threaded locking head 69, thereby creating shavings of the locking screw 41, and in particular of the threaded locking head 69. Alternatively still, when the internal locking surface 65 has a hardness substantially equal to that of the threaded locking head 69, cross-threading can cause one or both of 1) the locking screw 41, and in particular the threaded locking heads 69, to shave material from the bone plate 30, and in particular the internal locking surface 65, thereby creating shavings of the bone plate 30, and in particular of the internal locking surface 65, and 2) the bone plate 30, and in particular the internal locking surface 65, to shave material from the locking screw 41, and in particular the threaded locking head 69, thereby creating shavings of the locking screw 41, and in particular of the threaded locking head 69.

As will now be described with respect to the standard-type locking hole 47, the bone plate 30 is configured to capture shavings that are produced when threadedly mating the locking screw 41 to the bone plate 30.

The standard-type locking hole 47 and the standard-type locking bone screw 51 will now be described in more detail with respect to FIGS. 1-5 generally. With initial reference to FIGS. 1-4, the threaded internal locking surface 65 of the standard-type locking hole 47 can include an internal standard-type locking surface 71 and at least one helical thread 75 that extends out from the standard-type internal locking surface 71. Thus, the locking surface 71 can define at least one threaded surface 83. The at least one thread 75 can extend out from the threaded surface 83 in the locking hole 47. The at least one helical thread 75 is continuous along greater than one revolution about the central hole axis 45. Thus, the at least one helical thread 75 can be referred to as a standard-type helical thread. The at least one thread 75 can be configured as a single lead thread, a double lead thread, or any number of leads as desired. Otherwise stated, the bone plate body 31, and thus the bone plate 30, can include the internal standard-type locking surface 71 that at least partially defines the standard-type locking hole 47. For instance, the standard-type locking surface 71 can extend along the axial direction.

In this regard, the axial direction is used herein as a bi-directional term that includes both an axially inward direction from the outer surface 36 to the inner surface 34 of the bone plate 30, and an axially outward direction from the inner surface 34 to the outer surface 36. Thus, the directional term "axially inward" and derivatives thereof as used herein refers to a direction from the outer surface 36 toward the inner surface 34. Conversely, the terms "axially outward" and derivatives thereof as used herein refers to a direction from the inner surface 34 toward the outer surface 36. The axial direction, including the axially inward and axially outward directions, can be oriented along the central hole axis 45. Alternatively, the axial direction, including the axially inward and axially outward directions, can be oriented along a direction oblique to the central hole axis 45, for instance when used with reference to the locking surfaces 65 of the bone plate 30, and in particular the standard-type locking surface 71.

It should be appreciated that the description herein of the standard-type locking surface 71 and at least one thread 75 of the standard-type locking hole 47 can apply more generically with equal weight and effect to the threaded internal surface 65 of the threaded locking hole 44. The standard-type locking hole 47 is further configured to threadedly mate with the standard-type threaded head 56 of the standard-type locking bone screw 51. That is, the at least one thread 75 of the threaded internal standard-type locking surface 71 can threadedly purchase with the threaded at least one thread 63 of the external surface 55 of the head 56 of the standard-type locking screw 51. The central screw axis 53 of the standard-type locking screw 51 is at a predetermined orientation with respect to the central hole axis 45 of the standard-type locking hole 47, and at no other orientations with respect to the central hole axis 45. The predetermined orientation can be achieved when the central screw axis 53 is substantially coincident with or oblique to the central hole axis 45.

The external thread 63 of the external surface 55 of the head 56 of the standard-type locking screw 51 can be circumferentially continuous about the central screw axis 53. It should be appreciated, however, that the head 56 can be alternatively constructed in any manner desired so as to threadedly mate with the at least one thread 75 in the manner described herein. In one example, the external surface 55 of the head 56 of the standard-type locking screw 51 can be tapered radially inwardly as it extends along the axially inward direction. For instance, the external surface 55 of the head 56 of the standard-type locking screw 51 can be tapered linearly. Thus, the head 56 of the standard-type locking screw 51 can be conical in shape.

In this regard, the radial direction is used herein as a bi-directional term that includes both a radially inward direction toward the central hole axis 45, and a radially outward direction away from the central hole axis 45. Thus, the directional term "axially inward" and derivatives thereof as used herein refers to a direction toward the central hole axis 45. Conversely, the terms "radially outward" and derivatives thereof as used herein refer to a away from the central hole axis 45. The radial directions can be oriented perpendicular to the central hole axis 45, or can be oblique to the central hole axis 45.

The linear taper can define any suitable slope with respect to the central screw axis 53. The slope of the head 56 can be between 5 degrees and 25 degrees. For instance, the slope of the head 56 can be approximately 10 degrees. The terms "approximately" and "substantially" as used herein with respect to dimensions and angles takes into account manufacturing tolerances. Further, the terms "approximately" and "substantially" can include 10% greater than or less than the stated dimension or angle. Further, the terms "approximately" and "substantially" can equally apply to the specific value stated. The slope of the head 56 can extend along the crests of the at least one external thread 63. Alternatively or additionally, the slope of the head 56 can extend along the roots of the at least one external thread 63.

Referring now to FIGS. 3 and 4 in particular, the bone plate body 31, and thus the bone plate 30, can define a collection cavity 79. The collection cavity 79 interrupts the at least one thread 75 of the internal locking surface 71 along the axial direction. Thus, a first portion of the at least one thread 75 can extend axially outward with respect to the collection cavity 79, and a second portion of the at least one thread 75 can extend axially inward with respect to the collection cavity 79. The collection cavity 79 is configured to collect shavings that may be produced while the at least one thread 63 of the standard-type locking head 56 threadedly purchases with the at least one thread 75 of the internal surface 71 in the manner described above.

In one example, the collection cavity 79 can be configured as a collection recess 81 that is swept circumferentially about the central hole axis 45. In particular, the collection recess 81 can extend circumferentially alone or in combination with an axial directional component. The internal surface 71 defines a recessed collection surface 84 that is recessed radially outward with respect to the at least one threaded surface 83 so as to define the collection recess 81. The recessed collection surface .84 extends radially outward away from the central hole axis 45 with respect to the at least one threaded surface 83 so as to interrupt the at least one thread 75 along the axial direction. In one example, the recessed collection surface .84 can be unthreaded. The collection recess 81 can be configured in any manner as desired. In one example, the recessed collection surface .84 can be unthreaded and smooth.

The recessed collection surface 84, and thus the collection recess 81, can extend circumferentially along a circumferential length so as to divide at least a portion of the at least one thread 75 into a first or axially outer thread segment 75*a*, and a second or axially inner thread segment 75*b*. Accordingly, the recessed collection surface .84, and thus the collection recess 81, can divide the threaded surface 83 into a first or axially outer threaded surface segment 83*a* that carries the axially outer thread segment 75*a*, and a second or axially inner threaded surface segment 83*b* that carries the second thread segment 75*b*. The outer thread segment 75*a* and the inner thread segment 75*b* can lie along a common helical path. That is, the outer thread segment 75*a* lies along a respective outer helical path, the inner thread segment 75*b* lies along a respective inner helical path, and the outer helical path can be helically aligned with the inner helical path along the common helical path. Alternatively, the outer and inner thread segments 75*a* and 75*b* can lie on different helical paths that are parallel to each other. In one example, the collection surface 84, and thus the collection recess 81, can define an axial length greater than the pitch of each of the outer thread segment 75*a* and the inner thread segment 75*b*. For instance, the collection surface 84, and thus the collection recess 81, can define an axial length at least twice the pitch of each of the outer thread segment 75*a* and the inner thread segment 75*b*.

In one example, the circumferential length of the recessed collection surface .84, and thus of the collection recess 81, can extend at least 90 degrees circumferentially about the central hole axis 45. For instance, the circumferential length can extend at least 180 degrees about the central hole axis 45. In one example, the circumferential length can extend a full 360 degree revolution about the central hole axis 45. The recessed collection surface .84, and thus the collection recess 81, can extend continuously and uninterrupted along an entirety of the circumferential length about the central hole axis 45. Alternatively, it should be appreciated that the collection recess 81 can be segmented into one or more circumferential segments having circumferentially opposed terminal ends.

Referring now to FIGS. 3-4, the recessed collection surface .84 can define a first or axially outer end 84*a*, and a second or axially inner end 84*b* opposite the axially outer end 84*a*. The axially outer end 84*a* can define an interface with the axially outer threaded surface segment 83*a*, and the radially inner end 84*b* can define an interface with the axially inner threaded surface segment 83*b*. At least a portion of the recessed collection surface .84, up to an entirety of the recessed collection surface .84, can be concave along a plane that includes the central hole axis 45. For instance, the recessed collection surface .84 can be curved along the plane, though the recessed surface can define any suitable alterative shape along the plane as desired. Because at least a portion of the locking surface tapers radially inward as it extends axially inward, the axially inner end 84*b* can be offset with respect to the axially outer end 84*a* along the radially inward direction toward the central hole axis 45.

Further, the recessed collection surface .84 can be oriented along a respective plane that is oriented perpendicular to the central hole axis 45. Thus, the respective plane can intersect the helical path defined by the axially outer and inner thread segments 75*a* and 75*b*. For instance, an entirety of the axially outer end 84*a* can lie on a respective plane that is oriented perpendicular to the central hole axis 45. Further, the axially outer end 84*a* can extend along a circular path in the respective plane. Thus, in one example, the axially outer end 84*a* can be spaced a constant distance from the central hole axis 45 along the radial direction along an entirety of the length of the collection recess 81. Alternatively or additionally, an entirety of the axially inner end 84*b* can lie on a respective plane that is oriented perpendicular to the central hole axis 45. Further, the axially inner end 84*b* can extend along a circular path in the respective plane. Thus, in one example, the axially inner end 84*b* can be spaced a constant distance from the central hole axis 45 along the radial direction along an entirety of the length of the collection recess 81. Alternatively or additionally still, an entirety of a midline 86 of the recessed collection surface .84 can lie on a respective plane that is oriented perpendicular to the central hole axis 45. Further, the midline 86 can extend along a circular path in the respective plane. Thus, in one example, the midline 86 can be spaced a constant distance from the central hole axis 45 along the radial direction along an entirety of the length of the collection recess 81. The midline 86 can be equidistantly spaced between the radially outer end 84*a* and the radially inner end 84*b*. The midline 86 can define a radial depth that is spaced radially further from the central hole axis 45 than any other location of the recessed collection surface .84. Further, the radial depth of the collection recess 81 can be greater than the maximum height of the thread segments 75*a* and 75*b*.

The internal locking surface 71 can include a tapered lead-in surface 91 at the axially outer end of the standard-type locking hole 47. Further, the internal surface 71 can include a tapered undercut surface 93 at the axially inner end of the standard-type locking hole 47. The lead-in surface 91 can flare radially outward as it extends in the axially outward direction. The lead-in surface 91 can further be devoid of threads, and can be smooth. The lead-in surface 91 can extend circumferentially about the axially outer end of the standard-type locking hole 47. In one example, the lead-in surface 91 can extend circumferentially continuously and uninterrupted along a full revolution about the central hole axis 45. For instance, the lead-in surface 91 defines an axially outer end at the outer surface 36 of the bone plate 30. The lead-in surface 66 thus extends axially inward from its axially outer end to its axially inner end. The axially inner end of the lead-in surface 91 can be define an interface with the axially outer threaded surface segment 83*a*, and thus with the axially outer thread segment 75*a*.

The undercut surface 93 can flare radially outward as it extends in the axially inward direction. The undercut surface 93 can further be devoid of threads, and thus can be smooth. The undercut surface 93 can extend circumferentially about the axially inner end of the standard-type locking hole 47. In one example, the undercut surface 93 can extend circumferentially continuously and uninterrupted along a full revolution about the central hole axis 45. For instance, the undercut surface 93 can extend axially outward from the inner surface axially inner threaded surface segment 83*b*, and thus from the axially inner thread segment 75*b*. The undercut surface 93 can define an average diameter that is less than that of the lead-in surface 91.

Referring now to FIG. 5, the collection cavity 79, and thus the collection recess 81, can be configured to collect at least one shaving 88 that can be produced, for instance when the at least one external thread 63 of the head 56 of the standard-type locking screw 51 cross-threads with the at least one thread 75 of the bone plate 30 as the standard-type locking screw 51 is driven into the standard-type locking hole 47. For instance, when the threaded head 56 of the standard-type locking screw 51 is harder than the internal standard-type locking surface 71, cross-threading can cause the standard-type locking screw 51, and in particular the threaded heads 56, to shave material from the bone plate 30, such as from one or both the internal surface 71 and the at least one thread 75. The shaved material from the bone plate 30 can be referred to as plate shavings 90. Thus, the at least one shaving 88 can include one or more plate shavings 90.

It is envisioned that cross-threading can occur at the interface between the standard-type locking surface 71 and the external surface 55 of the threaded locking head 56. In particular, cross-threading can occur at the interface between the axially outer threaded surface segment 83*a*, such as the axially outer thread segment 75*a*, and the external surface 55 of the threaded locking head 56, for instance at the external thread 63. Alternatively or additionally, cross-threading can occur at the interface between the axially inner threaded surface segment 83*b*, such as the axially inner thread segment 75*b*, and the external surface 55 of the threaded locking head 56, for instance at the external thread 63. Therefore, plate shavings 90 can be produced from the threaded surface 83, for instance at the axially outer thread segment 75*a*. For instance, plate shavings 90 can be produced from the axially outer threaded surface segment 83*a*, such as the axially outer thread segment 75a. Alternatively or additionally, plate shavings 90 can be produced from the axially inner threaded surface segment 83b, such as the axially inner thread segment 75b.

Without being bound by theory, it is envisioned that plate shavings 90 produced from the axially outer threaded surface segments 83a can be driven axially, for instance, axially inwardly along the helical path, as the threaded head 56 travels axially inwardly along the helical path. In particular, when the plate shavings 90 are freely slidable with respect to the locking head 56, the plate shavings 90 can be driven axially inwardly into the collection recess 81, and thus the collection cavity 79. Further, without being bound by theory, it is envisioned that the plate shavings 90 produced from the axially inner threaded surface segments 83b can be driven axially outward, for instance along the helical path, as the threaded head 56 travels axially inward along the helical path. In particular, when the plate shavings 90 are broken off from the plate 30 and/or are pinched between the locking head 56 and the plate 30, and thus not freely slidable with respect to the locking head 56, the plate shavings 90 can be driven axially outwardly into the collection recess 91, and thus the collection cavity 79. Alternatively, if the plate shavings 90 produced from the axially inner threaded surface segments 83b are driven axially inward, then the plate shaving 90 would exit the bone plate at the bone-facing surface of the bone plate. Accordingly, the shaving is prevented from traveling to the soft tissue that may reside at a location adjacent the outer surface 36 of the bone plate 30.

As a result, at least one or more plate shavings 90 can be captured radially between the recessed collection surface 84 and the threaded head 56. Thus, the at least one captured plate shaving 90 is prevented from traveling out of the standard-type locking hole 47 of the bone plate 30 and into surrounding soft tissue, and can further be removed from the threaded interface between the threaded head 56 and the internal locking surface 71.

Alternatively, the bone plate 30 can be harder than the standard-type locking screw 51. Thus, the internal standard-type locking surface 71 can be harder than the threaded head 56 of the standard-type locking screw 51. Accordingly, cross-threading can cause one or both of the internal standard-type locking surface 71 and the at least one thread 75 to shave material from the standard-type locking screw 51, and in particular from one or both of the external surface 55 and at least one helical thread 63 of the standard-type threaded head 56. The shaved material from the standard-type locking screw 51 can be referred to as screw shavings 92. Thus, the at least one shaving 88 can include one or more screw shavings 92.

As described above, is envisioned that cross-threading can occur at the interface between the standard-type locking surface 71 and the external surface 55 of the threaded locking head 56. In particular, cross-threading can occur at the interface between the axially outer threaded surface segment 83a, such as the axially outer thread segment 75a, and the external surface 55 of the threaded locking head 56, for instance at the external thread 63. Alternatively or additionally, cross-threading can occur at the interface between the axially inner threaded surface segment 83b, such as the axially inner thread segment 75b, and the external surface 55 of the threaded locking head 56, for instance at the external thread 63.

Without being bound by theory, it is envisioned that screw shavings 92 can be driven axially, for instance axially inward along the helical path, as the threaded head 56 travels axially inward along the helical path. In particular, when the screw shavings 92 are broken off from the external surface 55, such as at the at least one thread 63, and/or are pinched between the locking head 56 and the plate 30, and thus not freely slidable with respect to the plate 30, the screw shavings 92 can be driven axially inward. Thus, screw shavings 92 produced at a location axially outward of the collection cavity can be driven axially inward into the collection recess 81, and thus the collection cavity 79. Further, without being bound by theory, it is envisioned that screw shavings 92 can be driven axially, for instance axially outward along the helical path, as the threaded head 56 travels axially inward along the helical path. In particular, when the screw shavings 92 are freely slidable with respect to the threaded internal surface 65 of the bone plate 30, the screw shavings 92 can be driven axially outward. Thus, screw shavings 92 produced at a location axially inward of the collection cavity 79 can be driven axially outward into the collection recess 81, and thus the collection cavity 79. Accordingly, the screw shaving 92 is captured radially between the recessed collection surface .84 and the threaded head 56. Alternatively, if the screw shavings 92 produced at the location axially inward of the collection cavity 79 travel axially inward, then the screw shavings 92 would exit the bone plate at the bone facing inner surface 34. Thus, the screw shaving 92 is prevented from traveling through the bone plate 30 at the outer surface 36 and is thus prevented from traveling to the surrounding soft tissue. It should also be appreciated that the screw shaving 92 is removed from the threaded interface between the threaded head 56 and the internal locking surface 71.

Alternatively still, when the internal standard-type locking surface 71 has a hardness substantially equal to that of the threaded locking head 56, cross-threading can cause one or both of 1) the standard-type locking screw 51, and in particular the threaded locking head 56, to shave material from the bone plate 30 so as to produce the plate shaving 90 and 2) the bone plate 30, and in particular the internal standard-type locking surface 71, to shave material from the standard-type locking screw 51, and in particular from the threaded locking head 56, so as to produce the screw shaving 92. The shavings 90 and 92 can travel into the collection cavity 79 or out the inner bone-facing surface 34 in the manner described above. Thus, it is appreciated that the at least one shaving 88 can include one or more plate shaving 90 and no screw shavings 92, one or more screw shaving 92 and no plate shavings, or a combination of one or more plate shaving 90 and one or more screw shaving 92.

As described above, while the standard-type locking hole 47 can include the collection cavity 79 that is configured to retain at least some of the shavings that are produced when the head 56 of the standard-type locking screw 51 is threadedly mated to the bone plate 30, it is recognized that the variable angle locking hole 54 can further include the collection cavity 79. The collection recess 81, and thus the collection cavity 79, can be positioned anywhere along the internal surface 71 of the bone plate 30 as desired. For instance, in one example, the collection recess 81 can be positioned such that the internal surface 71 defines at least one revolution of the at least one thread 75 between the collection recess 81 and the outer surface 36 of the bone plate 30. Alternatively or additionally, the collection recess 81 can be positioned such that the internal surface 71 defines at least one revolution of the at least one thread 75 between the collection recess 81 and the inner surface 34 of the bone plate 30.

The VA locking hole 54 will now be described in more detail with respect to FIGS. 6-9. The threaded internal locking surface 65 of the VA locking hole 54 can be referred to as a threaded internal surface 39, which can be configured as an internal variable angle locking surface. The internal surface 39 of the bone plate 30 extends from the outer surface 36 to the inner surface 34 so as to define the VA locking hole 54 that extends from the outer surface 36 to the inner surface 34. In particular, the VA locking hole 54 extends along the central hole axis 45. The central hole axis 45 can be oriented along the transverse direction T. Thus, the central hole axis 45 can be oriented normal to each of the inner surface 34 and the outer surface 36. It should be appreciated, of course, that the central hole axis 45 can be oriented in any suitable direction as desired, including a direction oblique to the transverse direction T.

The internal surface 39, and thus the bone plate 30, can define a plurality of threaded regions 62 that carry at least one thread 46. The internal surface 39, and thus the bone plate 30, can further define a plurality of relief regions 64 that are disposed circumferentially between respective adjacent ones of the threaded regions 62. Thus, the threaded regions 62 and the relief regions 64 can be alternatingly arranged with each other circumferentially about the central hole axis 45. The threaded regions 62 and the relief regions 64 are configured such that the VA locking screws 43 are configured to threadedly purchase with the internal surface 39 at the threaded regions 62 without threadedly purchasing with the internal surface 39 at the relief regions 64.

In one example, the at least one thread 46 projects out from the internal surface 39 at the threaded regions 62 into the VA locking hole 54 generally toward the central hole axis 45. The at least one thread 46 can be monolithic with the internal surface 39. The at least one thread 46 can extend along a thread path. The thread path can be a helical thread path. In one example, the at least one thread 46 can be a single lead thread, a double lead thread, or any suitably constructed thread as desired. The internal surface 39 can further define a recess such as a relief recess 48 at each of the relief regions 64. The relief recesses 48 can circumferentially interrupt the at least one thread 46 so as to define a plurality of thread segments 60 of the at least one thread 46. Axially aligned ones of the thread segments can combine to define a plurality of threaded columns 50. Thus, it can be said that the threaded columns 50 are defined by thread segments 60. Because the at least one thread 46 can extend along a helical thread path, the threaded columns 50 can have different numbers of thread segments 60. The relief recesses 48 and the columns 50 can be alternatingly arranged with each other circumferentially about the central hole axis 45. The at least one relief recess 48 is offset with respect to the columns 50 of thread segments 60 in a radially outward direction. The internal surface 39 can be said to define a relief surface 61 that at least partially defines the relief recesses 48.

The axial direction is defined as a direction between the outer surface 36 and the inner surface 34 of the bone plate 30. Thus, the directional term "axially inward" and derivatives thereof as used herein refers to a direction from the outer surface 36 toward the inner surface 34. Conversely, the terms "axially outward" and derivatives thereof as used herein refers to a direction from the inner surface 34 toward the outer surface 36. The axial direction, including the axially inward and axially outward directions, can be oriented along the central hole axis 45. Alternatively, the axial direction, including the axially inward and axially outward directions, can be oriented along a direction oblique to the central hole axis 45, for instance when used with reference to the locking surfaces 65 of the bone plate 30, and in particular the internal VA locking surface 39.

The relief recesses 48 can have a radial depth sufficient such that the relief surface 61 is recessed with respect to the internal surface 39 at the columns 50 along the radially outward direction. That is, the relief surface 61 can define a radial distance from the central hole axis 45 that is greater than the radial distance from the central hole axis 45 to the major diameter of the at least one thread 46 of the columns 50. Therefore, during operation, the VA screw head 59 of the VA locking bone screw 43 that threadedly purchases with the internal surface 39 at the columns 50 of thread segments 60 are spaced radially inward from the internal surface 39 at the relief recess 48. The relief surfaces 61 can be devoid of the thread 46. For instance, the relief surfaces 61 can be unthreaded and smooth. The thread segments 60 of each of the columns 50 are spaced from each other in the axial direction so as to define interstices that receive corresponding external threads 94 of the VA screw head 59.

The thread segments 60 of each of the columns 50 can be circumferentially offset from the thread segments 60 of the other ones of the columns 50. Further, adjacent ones of the circumferentially spaced thread segments 60 can be separated by a respective common one of the relief recesses 48. Thus the thread segments 60 of each column 50 can be aligned with the thread segments 60 of one or both adjacent column 50 along the thread path. Because the thread path can be helical, the thread segments 60 can be aligned with the thread segments 60 of an adjacent one of the columns 50 along a helical path. In one example, each of the thread segments 60 of a respective one of the columns 50 is aligned along the thread path with 1) one the thread segments 60 a first adjacent column 50, and 2) one the thread segments 60 of a second adjacent column 50. Thus, the respective one of the columns 50 is disposed circumferentially between the first adjacent column 50 and the second adjacent column 50. Further, the thread segments 60 of the respective one of the columns 50 is disposed between the first one of the thread segments 60 and the second one of the thread segments 60 with respect to the axial direction.

In one example, the bone plate 30 can include four recesses 48 and four columns 50. However, it is appreciated that the bone plate 30 can include any number of recesses 48, greater than one, as desired, and as many corresponding columns 50, greater than one, so as to define the variable angle locking hole 54 of the type described herein. Further, the relief recesses 48 can be substantially (within manufacturing tolerance) identical to each other. Similarly, the columns 50 can be substantially (within manufacturing tolerance) identical to each other. Thus, the relief recesses 48 can be circumferentially equidistantly spaced from each other about the central hole axis 45. Similarly, the columns 50 can be circumferentially equidistantly spaced from each other about the central hole axis 45. Alternatively, the relief recesses 48 can be circumferentially spaced from each other at a variable distance about the central hole axis 45. Similarly, the columns 50 can be circumferentially spaced from each other at a variable distance about the central hole axis 45.

In one example, the relief surface 61 extends along a circular path along the plane that is oriented normal to the central hole axis 45. Thus, the curvature can be defined by a radius that is swept in a plane oriented normal to the central hole axis 45. Further, the radius can be smaller than the radius from the central hole axis 45 to the internal surface 39. While the threaded regions 62 include respective columns 50 of threaded segments 60, it should be appreciated that the internal surface 39 need not be threaded along its entirety at locations axially aligned with the columns 50. For instance, the internal surface 39 can include a tapered lead-in surface 66 at the axially outer end of the VA locking hole 54. Further, the internal surface 39 can include a tapered undercut surface 68 at the axially inner end of the VA locking hole 54.

The lead-in surface 66 can flare radially outward as it extends in the axially outward direction. The lead-in surface 66 can further be devoid of threads. For instance, the lead-in surface 66 can be smooth. The lead-in surface 66 can extend circumferentially continuously and uninterrupted along a full revolution about the central hole axis 45. In one example, the lead-in surface 66 can define an axial length at locations aligned with the columns 50 that are greater than the axial length of the lead-in surface at locations aligned with the relief recesses 48. The lead-in surface 66 defines an axially outer end at the outer surface 36 of the bone plate 30. The lead-in surface 66 thus extends axially inward from its axially outer end to its axially inner end. At locations axially aligned with the columns 50, and thus axially aligned with the threaded regions 62, the axially inner end of the lead-in surface 66 can be defined by an axially outermost one of the thread segments 60 of the columns 50. At locations axially aligned with the relief surfaces 61, and thus axially aligned with the relief regions 64, the axially inner end of the lead-in surface 66 can be defined as an intersection between the lead-in surface 66 and the relief surface 61. The intersection can be defined at the axially outermost end of the relief surfaces 61.

The outer surface 36 of the bone plate 30 can define an axially outer perimeter 70 of an axially outer opening 72 to the VA locking hole 54. Thus, the lead-in surface 66 or segments of the lead-in surface 66 can axially inward from the perimeter 70. In one example, the perimeter 70 can define a circle, though it should be appreciated that the outer perimeter 70 can define different geometric shapes as desired. A circle may be preferable in some examples because, as described in more detail below, the VA locking screw 43 can threadedly purchase with the columns 50 at an angle relative to the central hole axis 45 within a range of angles at which the head 33 of the VA locking screw 43 can threadedly purchase with the columns 50. Thus, the outer perimeter 70 can surround a portion of the VA threaded head 59 when the VA threaded head 59 is purchased with the columns 50 at an angle within the range of angles. In one example, the relief surfaces 61 can extend from the inner surface 34 to the lead-in surface 66. The shaft can extend into the relief recesses when the VA locking screw 43 is angulated with respect to the central hole axis 45 and threadedly purchased with the bone plate 30 in the VA locking hole 54.

The undercut surface 68 can flare radially outward as it extends in the axially inward direction. The undercut surface 68 can further be devoid of the at least one thread 46. For instance, the undercut surface 68 can be smooth. The undercut surface 68 can extend circumferentially about the axially inner end of the VA locking hole 54 at locations aligned with the columns 50. Alternatively, the undercut surface 68 can extend circumferentially continuously and uninterrupted along a full revolution about the central hole axis 45. For instance, the undercut surface 68 can extend axially outward from the inner surface 34 of the bone plate 30. Thus, the undercut surface 68 has an axially inner end at the inner surface 34. The undercut surface 68 has an axially outer end opposite the axially inner end along the axial direction. At locations axially aligned with the columns 50, and thus axially aligned with the threaded regions 62, the axially outer end of the undercut surface 68 can be disposed at the axially innermost thread segment 60 of the columns 50.

The inner surface 34 of the bone plate 30 can define an axially inner perimeter of an axially inner opening 76 to the VA locking hole 54. In one example, the inner perimeter can define a circle, though it should be appreciated that the inner perimeter can define different geometric shapes as desired. A circle may be preferable in some examples because, as described in more detail below, a VA locking screw 43 can threadedly purchase with the columns 50 at an angle relative to the central hole axis 45 within a range of angles at which the VA threaded head 59 of the VA locking screw 43 can threadedly purchase with the columns 50. The range of angles can be disposed within a cone. Thus, the undercut surface 68 or segments of the undercut surface 68 can provide clearance for the screw shaft at different angles within the range of angles.

It should be appreciated that the columns 50 can extend from the lead-in surface 66 to the undercut surface 68. Further, the columns 50 can taper radially inward toward the central hole axis 45 as they extend axially inward. In one example, the columns 50 can extend linearly along the axially inward direction from the lead-in surface 66 to the undercut surface 68. Further, the VA locking hole 54 can be constructed such that no portion of the internal surface 39 extends radially inward of the columns 50. Therefore, the VA locking screw 43 described herein can threadedly purchase within the columns 50 without contacting any other surface except for the columns 50 and the undercut surface 68 when the VA locking screw 43 is fully angulated. The relief surfaces 61 can also extend from the lead-in surface 66 to the undercut surface 68. Further, the relief surfaces 61 can taper radially inward toward the central hole axis 45 as they extend axially inward. In one example, the relief surfaces 61 can extend linearly along the axial direction from the lead-in surface 66 to the undercut surface 68.

The VA locking hole 54 is configured to receive a the VA locking screw 43 that is configured to threadedly mate with the bone plate 30 in the VA locking hole 54 at different orientations with respect to the central hole axis 45. The VA threaded head 59 (see FIG. 1) can be constructed in accordance with any embodiment as described in U.S. Pat. No. 8,574,268, the disclosure of which is hereby incorporated by reference as if set forth in its entirety herein. Thus, it is appreciated that the VA threaded head 59 of the VA locking screw 43 can define an external surface and at least one external thread 78 that extends from the external surface. The VA threaded head 59 of the VA locking screw 43 have a curved outer surface, which can be convex in one example. In particular, the outer surface can be spherical. Further, the external thread 78 of the VA threaded head 59 of the VA locking screw 43 can be circumferentially continuous about the central screw axis 53. It should be appreciated, however, that the VA threaded head 59 can be alternatively constructed in any manner desired so as to threadedly mate with the at least one thread 46 in the manner described herein.

Otherwise stated, the VA locking screw 43 is configured to be inserted into the VA locking hole 54 such that the central screw axis 53 is at one of a plurality of angles with respect to the central hole axis 45 within a range of angles at which the VA threaded head 59 is configured to threadedly mate with the at least one thread 46 in the VA locking hole 54. For instance, the VA locking screw 43 is configured to be inserted into the VA locking hole 54 such that the central screw axis 53 is at one of a plurality of angles within a range of angles defined by the central screw axis 53 and the central hole axis 45 at which the VA threaded head 59 is configured to threadedly mate with each of the columns 50. The range of angles can be disposed within a cone that is centered about the central hole axis 45. Thus, the range of angles can be disposed within a cone of up to thirty degrees. The range of angles can be measured as 15 degrees with respect to the central hole axis 45. The central hole axis 45 can define the center of the cone. Thus, the VA threaded head 59 of the VA locking screw 43 can mate with the bone plate 30 in the manner described herein both when central screw axis 53 of the VA locking screw 43 is coincident with the central hole axis 45 and when the central screw axis 53 of the VA locking screw 43 is at any other angle with respect to the central hole axis 45 within the range of angles.

Thus, it can be said that the at least one thread 46 is configured to threadedly mate with the VA threaded head 59 while the VA locking screw 43 is inserted into the VA locking hole 54 such that the central screw axis 53 is oriented at a first angle with respect to the central hole axis 45, and the at least one thread 46 is further configured to threadedly mate with the VA threaded head 59 when the VA locking screw 43 is inserted into the VA locking hole 54 such that the central screw axis 53 is oriented at a second angle with respect to the central hole axis 45 that is different than the first angle. At least one or both of the first and second angles can be non-zero angles. Alternatively, the central screw axis 53 can be coincident with the central hole axis 45 in one of the orientations in the range of orientations.

Figure 10:
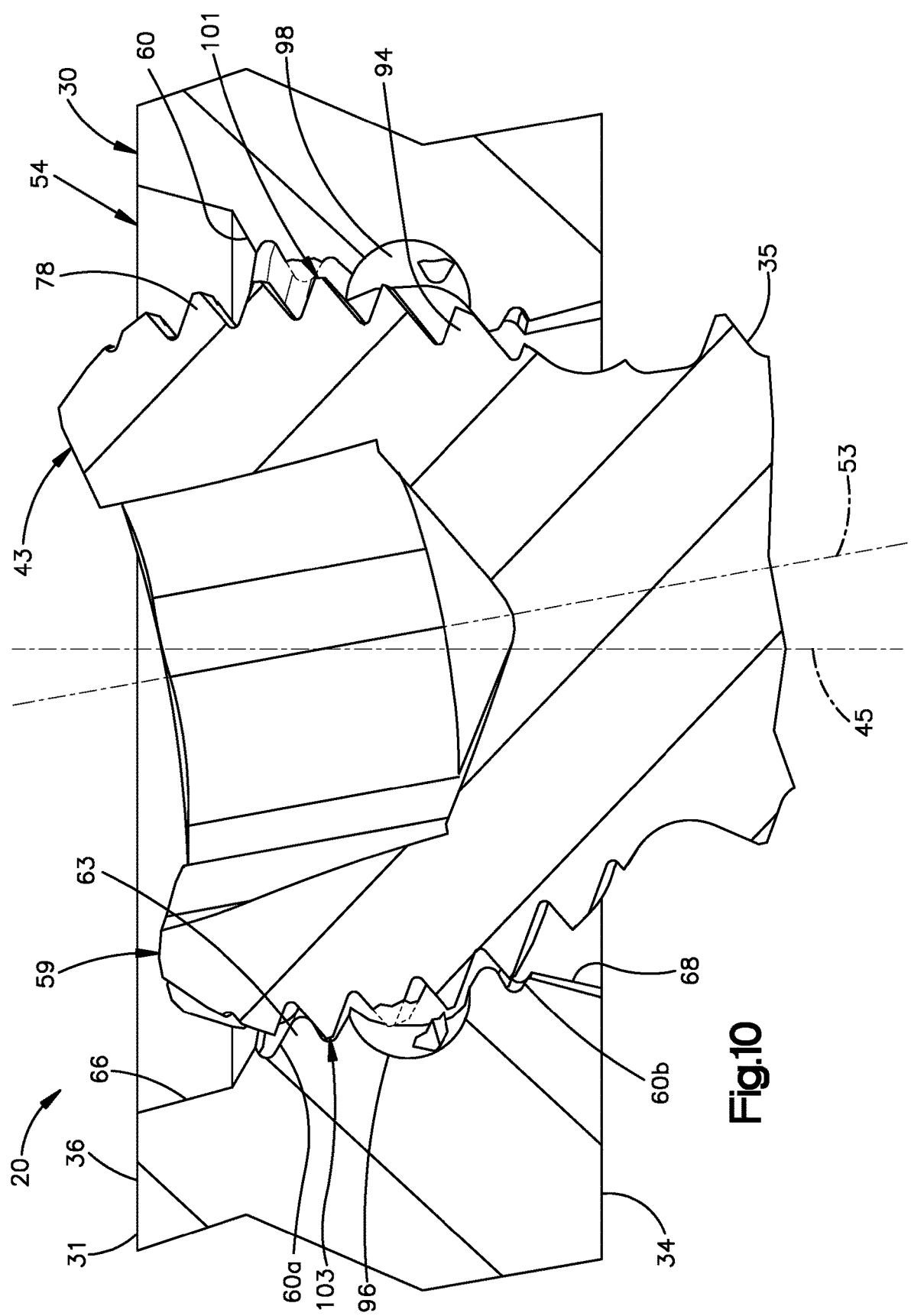
FIG. 10 is a sectional side elevation view of the portion of the bone plate illustrated in FIG. 9, but shown with the variable-angle bone screw illustrated in FIG. 1 being driven into the variable-angle screw hole and producing shavings.

Referring to FIG. 10, the VA locking hole 54 is configured to receive the VA locking screw 43 such that respective ones of the columns 50 threadedly purchase with the externally threaded VA threaded head 59 of the VA locking screw 43 when the central screw axis 53 and the central hole axis 45 define any angle within the range of angles that are disposed within the cone. Thus, the thread segments 60 of the columns 50 and the external thread 78 of the VA threaded head 59 of the VA locking screw 43 can be configured to threadedly purchase with each other. In one example, the external thread 78 of the VA threaded head 59 of the VA locking screw 43 defines a respective thread angle, and the thread segments 60 of the columns 50 define a respective thread angle. In one example, the thread angle of the thread segments 60 can be greater than the thread angle of the external thread 78 of the VA threaded head 59 of the VA locking screw 43. Alternatively, the thread angle of the thread segments 60 can be less than the thread angle of the external thread 78 of the VA threaded head 59 of the VA locking screw 43. Alternatively still, the thread angle of the thread segments 60 can be substantially equal to the thread angle of the external thread 78 of the VA threaded head 59 of the VA locking screw 43.

The at least one thread 46 of the VA hole 54 and the at least one external thread 78 of the VA threaded head 59 are defined prior to insertion of the VA locking screw 43 into the VA locking hole 54. That is, the internal surface 39 is not designed or configured to cut or form threads into the VA threaded head 59. Similarly, the VA threaded head 59 is not designed or configured to cut or form threads into the internal surface 39. It is contemplated, however, as described above, that in the event of cross-threading while locking the VA locking screw 43 in the VA locking hole 54, the VA locking hole 54 is configured to contain the shavings.

In particular, referring to FIGS. 6-9 in particular, the bone plate body 31, and thus the bone plate 30, can define a collection cavity 96. The collection cavity 96 interrupts the thread segments 60 at least one of the columns 50 up to all of the columns 50 along the axial direction. Thus, a first portion of the at least one thread 46 can extend axially outward with respect to the collection cavity 96, and a second portion of the at least one thread 75 can extend axially inward with respect to the collection cavity 96. The collection cavity 96 can be configured to collect shavings that may be produced while the external at least one thread 78 of the VA locking head 59 is threadedly purchases with respective ones of the thread segments 60 of the columns in the manner described above.

In one example, each collection cavity 96 can be configured as a collection recess 98 that is swept circumferentially about the central hole axis 45. In particular, the collection recess 98 can extend circumferentially alone or in combination with an axial directional component. The internal surface 39 defines a recessed collection surface 100 that is recessed radially outward with respect to the threaded regions 62 so as to define the collection recess 98. The recessed collection surface 100 extends radially outward away from the central hole axis 45 with respect to the threaded regions 62 so as to interrupt the thread segments 60 of the columns 50 along the axial direction. In one example, the recessed collection surface 100 can be unthreaded. The collection recess 98 can be configured in any manner as desired. In one example, the recessed collection surface 100 can be unthreaded and smooth.

For instance, the recessed collection surface 100, and thus the collection recess 98, can extend circumferentially along a circumferential length so as to divide the thread segment 60 of each of the columns 50 into a first or axially outer thread segment 60a, and a second or axially inner thread segment 60b. Accordingly, the recessed collection surface 100, and thus the collection recess 98, can divide the threaded regions 62 into a first or axially outer threaded surface segment 62a that carries the axially outer thread segment 60a, and a second or axially inner threaded surface segment 62b that carries the axially inner thread segment 60b. The outer thread segments 60a of adjacent columns 50 can lie along a common outer helical path. Similarly, the inner thread segments 60b of adjacent columns 50 can lie along a common inner helical path. The first and second common helical paths can be helically aligned with each other. Alternatively, the outer and inner thread segments 60a and 60b can lie on different helical paths that are parallel to each other. In one example, the collection surface 100, and thus the collection recess 98, can define an axial length greater than the pitch of each of the outer thread segment 60a and the inner thread segment 60b. For instance, the collection surface 100, and thus the collection recess 98, can define an axial length at least twice the pitch of each of the outer thread segment 60a and the inner thread segment 60b.

In one example, the circumferential length of the recessed collection surface 100, and thus of the collection recess 98, can extend at least 90 degrees circumferentially about the central hole axis 45. For instance, the circumferential length can extend at least 180 degrees about the central hole axis 45. In one example, the circumferential length can extend a full 360 degree revolution about the central hole axis 45.

The recessed collection surface 100 can define a first or axially outer end 100a, and a second or axially inner end 100b opposite the axially outer end 100a. The axially outer end 100a can define an interface with the axially outer threaded surface segment 62a, and the radially inner end 100b can define an interface with the axially inner threaded surface segment 62b. At least a portion of the recessed collection surface 100, up to an entirety of the recessed collection surface 100, can be concave along a plane that includes the central hole axis 45. For instance, the recessed collection surface 100 can be curved along the plane, though the recessed surface can define any suitable alterative shape along the plane as desired. Because at least a portion of the threaded region 62 of the internal surface 39 tapers radially inward as it extends axially inward, the axially inner end 100*b* can be offset with respect to the axially outer end 100*a* along the radially inward direction toward the central hole axis 45.

Further, the recessed collection surface .84 can be oriented along a respective plane that is oriented perpendicular to the central hole axis 45. Thus, the respective plane can intersect the helical path defined by the first and second thread segments 60*a* and 60*b*. For instance, an entirety of the axially outer end 100*a* can lie on a respective plane that is oriented perpendicular to the central hole axis 45. Further, the axially outer end 100*a* can extend along a circular path in the respective plane. Thus, in one example, the axially outer end 100*a* can be spaced a constant distance from the central hole axis 45 along the radial direction along an entirety of the length of the collection recess 98. Alternatively or additionally, an entirety of the axially inner end 100*b* can lie on a respective plane that is oriented perpendicular to the central hole axis 45. Further, the axially inner end 100*b* can extend along a circular path in the respective plane. Thus, in one example, the axially inner end 100*b* can be spaced a constant distance from the central hole axis 45 along the radial direction along an entirety of the length of the collection recess 98.

Alternatively or additionally still, an entirety of a midline 102 of the recessed collection surface 100 can lie on a respective plane that is oriented perpendicular to the central hole axis 45. Further, the midline 102 can extend along a circular path in the respective plane. Thus, in one example, the midline 102 can be spaced a constant distance from the central hole axis 45 along the radial direction along an entirety of the length of the collection recess 98. The midline 102 can be equidistantly spaced between the axially outer end 100*a* and the axially inner end 100*b*. The midline 102 can define a radial depth that is spaced radially further from the central hole axis 45 than any other location of the recessed collection surface 100. Further, the radial depth of the collection recess 98 can be greater than the maximum height of the thread segments 60*a* and 60*b*.

Further, the radial depth of the recessed collection surface 100 can be greater than circumferentially outer portions of the relief surfaces 61, but less than circumferentially middle portions of the relief surfaces 61 that are disposed circumferentially between the circumferential outer portions of the relief surfaces 61. Accordingly, the recessed collection surface 100, and thus also the collection recess 98, can define a plurality of segments 104. In particular, each segment 104 can extend from a circumferentially outer portion of a first one of the relief surfaces 61 that is adjacent a select one of the columns 50, can extend across an entirety of the select one of the columns 50, and can terminate at a second one of the relief surfaces 61 that is adjacent the select one of the columns 50. Each segment 104 thus has a first terminal end 104*a* that is disposed at an intersection with the first one of the relief surfaces 61, and a second terminal end 104*b* circumferentially opposite the first terminal end 104*a* that is disposed at an intersection with the second one of the relief surfaces 61. The select one of the columns 50 is disposed between the first and second ones of the relief surfaces 61 along the circumferential direction. It is thus appreciated that the collection recess 98, and thus the collection cavity 96, can be open to the relief recesses 48.

Each segment 104 can extend continuously and uninterrupted along the select one of the columns 50 so as to divide an entirety of the column into the axially outer threaded surface segment 62*a* and the axially inner threaded surface segment 62*b*. Alternatively, the radial depth of the recessed collection surface 100, and thus the collection recess 98, can be greater than that of the relief surface 61. Accordingly, the recessed collection surface 100 extend continuously and uninterrupted along an entirety of the circumferential length about the central hole axis 45.

Referring now to FIG. 10, the VA locking head 59 defines a first or axially outwardly-facing side 101 and a second side or axially inwardly-facing side 103 that is opposite the first side 103. In particular, at least 5% more of the first side 101 than the second side 103 is disposed axially outward of a plane that is oriented perpendicular to the central hole axis 45 and extends through the VA locking head 59. Similarly, at least 5% more of the second side 103 than the first side 101 is disposed axially inward of the plane.

The collection cavity 96, and thus the collection recess 98, can be configured to collect at least one shaving 88 that can be produced, for instance when the at least one external thread 78 of the VA locking head 59 cross-threads with the at least one thread 46 of the bone plate 30 as the VA locking screw 43 is driven into the VA locking hole 54. For instance, when the threaded head 59 of the VA locking screw 43 is harder than the internal VA surface 39, cross-threading can cause the VA locking screw 43, and in particular the threaded head 59, to shave material from the bone plate 30 in the VA locking hole 54. For instance, the threaded head 59 can shave material from the one or both of the threaded region 62 and the at least one thread segment 60 of the columns 50, thereby creating plate shavings 90. Thus, the at least one shaving 88 can include one or more plate shaving 90.

It is envisioned that cross-threading can occur in one or more of the axially outer thread segments 60*a*, alone or in combination with one or more of the axially outer threaded surface segment 62*a*. Therefore, plate shavings 90 can be produced from one or both of the axially outer thread segments 60*a* and the axially outer threaded surface segment 62*a*. Alternatively or additionally, it is envisioned that cross-threading can occur in one or more of the axially inner thread segment 60*b* alone or in combination with the axially inner threaded surface segments 62*b*. Therefore, plate shavings 90 can be produced from one or both of the axially inner thread segments 60*b* and the axially inner threaded surface segment 62*b*.

Without being bound by theory, it is envisioned that plate shavings 90 produced from one or both of the axially outer thread segments 60*a* and the axially outer threaded surface segment 62*a* can be driven axially inward, for instance, along the helical path, as the threaded head 56 travels axially inwardly along the helical path. In particular, the portion of one or both of the axially outer thread segments 60*a* and the axially outer threaded surface segment 62*a* that are engaged with the first side 101 of the VA locking head 59 can be driven axially inwardly into the collection recess 98, and thus into the collection cavity 96. Further, without being bound by theory, it is envisioned that plate shavings 90 produced from one or both of the axially inner thread segments 60*b* and the axially inner threaded surface segment 62*b* can be driven axially outward, for instance, along the helical path, as the threaded head 56 travels axially inwardly along the helical path. In particular, the portion of one or both of the axially inner thread segments 60*b* and the axially outer threaded surface segment 62*b* that are engaged with the second side 103 of the VA locking head 59 can be driven axially inwardly into the collection recess 98, and thus into the collection cavity 96. Accordingly, at least a portion of the plate shaving 90 up to an entirety of the plate shaving 90 can be captured radially in the gap between the recessed collection surface 100 and the threaded head 56.

In some examples, it is envisioned that plate shavings 90 produced from of the axially outer thread segments 60*a* and the axially outer threaded surface segment 62*a* can travel circumferentially into one of the relief recesses 48, which can be open to the collection recess 98. Further, it is envisioned that plate shavings 90 produced from of the axially inner thread segments 60*b* and the axially inner threaded surface segment 62*b* can travel circumferentially into one of the relief recesses 48, which can be open to the collection recess 98. The plate shavings 90 can remain in the relief recess 48, or a portion up to all of the plate shaving can travel from the relief recess 48 to the collection recess 98, and thus into the collection cavity 96. Accordingly, the the plate shaving 90 can be captured in the gap that extends radially between the internal surface 39 and the VA locking head 59. For instance, at least a portion of the plate shaving 90 can be captured radially in the gap between the recessed collection surface 100 and the threaded head 56. Alternatively or additionally, at least a portion of the plate shaving 90 can be captured radially between the relief surface 61 and the threaded head 56. Thus, the plate shaving 90 is prevented from traveling through the bone plate 30, and further is removed from the threaded interface between the threaded VA head 59 and the internal surface 39.

While the VA screw 43 can be harder than the bone plate 30 as described above, it should be appreciated that the bone plate 30 can alternatively be harder than the VA screw 43. Thus, the internal surface 39 and thread segments 60 can be harder than the threaded VA locking head 59. Accordingly, cross-threading can cause one or both of the internal surfaces 39 and thread segments 60 to shave material from the VA locking screw 43, and in particular from one or both of the external surface of the VA head 59 and the at least one external thread 78. The shaved material from the VA locking screw 43 can be referred to as screw shavings 92. Thus, the at least one shaving 88 can include one or more screw shaving 92.

Further, as described above, it is envisioned that cross-threading can occur at the interface between the axially outer thread segment 60*a* and the internal surface 39. Alternatively or additionally, it is envisioned that cross-threading can occur at the interface between the axially inner thread segment 60*b* and the internal surface 39. In one example, without being bound by theory, it is envisioned that as the second side 103 of the threaded VA head 59 travels axially inwardly along the helical path defined by the axially outer thread segment 60*a*, the screw shaving 92 can be driven axially inward along the helical path of the axially outer thread segment 60*a* until it is delivered into the collection cavity 96. In some examples, the screw shaving 92 can travel circumferentially into one of the relief recesses 48, which can be open to the collection recess 98 as described above. Thus, at least a portion of the screw shaving 92 can be captured radially in the gap between the internal surface 39 and the threaded VA locking head 59. For instance, at least a portion of the screw shaving 92 can be captured radially in the gap between the recessed collection surface 100 and the threaded head 59. Alternatively or additionally, at least a portion of the screw shaving 92 can be captured radially between the relief surface 61 and the threaded head 59. Thus, the screw shaving 92 can be prevented from traveling through the bone plate 30. Further, the screw shaving can be removed from the threaded interface between the threaded VA head 59 and the internal surface 39.

Alternatively or additionally, as the first side 101 of the threaded VA head 59 travels axially inwardly along the helical path defined by the axially inner thread segment 60*b*, it is envisioned that the screw shaving 92 can be driven axially outward along the helical path of the axially inner thread segment 60*b* until it is delivered into the collection cavity 96. In some examples, the screw shaving 92 can travel circumferentially into one of the relief recesses 48, which can be open to the collection recess 98 as described above. Thus, at least a portion of the screw shaving 92 can be captured radially in the gap between the internal surface 39 and the threaded VA locking head 59. For instance, at least a portion of the screw shaving 92 can be captured radially in the gap between the recessed collection surface 100 and the threaded head 59. Alternatively or additionally, at least a portion of the screw shaving 92 can be captured radially between the relief surface 61 and the threaded head 59. Thus, the screw shaving 92 can be prevented from traveling through the bone plate 30. Further, the screw shaving can be removed from the threaded interface between the threaded VA head 59 and the internal surface 39.

Alternatively still, when the hardness of the internal surface 39 can be substantially equal to that of the external surface of the threaded VA locking head 59, cross-threading can cause one or both of 1) the VA screw 43, and in particular the threaded head 59, to shave material from the bone plate 30 so as to produce the plate shaving 90 and 2) the bone plate 30, and in particular the thread segments 60, to shave material from the VA locking screw 59, and in particular from the VA locking head 59, so as to produce the screw shaving 92. The shavings 90 and 92 can be delivered into the collection cavity 96 in the manner described above. Thus, it is appreciated that the at least one shaving 88 can include one or more plate shaving 90 and no screw shavings 92, one or more screw shaving 92 and no plate shavings, or a combination of one or more plate shaving 90 and one or more screw shaving 92.

Although the disclosure has been described in detail, it should be understood that various changes, substitutions, and alterations can be made herein without departing from the spirit and scope of the invention as defined by the appended claims. Moreover, the scope of the present disclosure is not intended to be limited to the particular embodiments described in the specification. As one of ordinary skill in the art will readily appreciate from that processes, machines, manufacture, composition of matter, means, methods, or steps, presently existing or later to be developed that perform substantially the same function or achieve substantially the same result as the corresponding embodiments described herein may be utilized according to the present disclosure.

What is claimed:

1. A bone plate configured to receive a locking bone screw, the bone plate comprising:
    an inner surface configured to face the underlying bone, and an outer surface opposite the inner surface along an axial direction; and
    a threaded internal locking surface that extends between the outer surface and the inner surface so as to define a locking hole that is oriented along a central hole axis, wherein the threaded internal locking surface is defined prior to insertion of the locking bone screw in the locking hole, and the threaded internal locking surface defines a collection cavity disposed between the outer surface and the inner surface, wherein the collection cavity is configured to collect a shaving that is produced from one of the bone plate and the locking bone screw while the locking bone screw is threadedly mated with the bone plate, and wherein the threaded internal locking surface defines at least one thread that is configured to threadedly mate with a threaded head of the locking bone screw, and the collection cavity interrupts the at least one thread.

2. The bone plate as recited in claim 1, wherein a first portion of the at least one thread extends axially outward with respect to the collection cavity, and a second portion of the at least one thread extends axially inward with respect to the collection cavity.

3. The bone plate as recited in claim 1, wherein the collection cavity is configured as a collection recess that is swept circumferentially about the central hole axis.

4. The bone plate as recited in claim 3, wherein the at least one thread is continuous along greater than one revolution about the central hole axis.

5. The bone plate as recited in claim 3, wherein the at least one thread is configured to threadedly purchase with the locking bone screw both when the locking bone screw is oriented coincident with the central hole axis and when the locking bone screw is at an angle relative to the central hole axis within a range of angles at which the locking bone screw is configured to threadedly purchase with the at least one thread.

6. The bone plate as recited in claim 5, wherein the threaded internal locking surface defines a plurality of threaded regions that carry the at least one thread, and further defines a plurality of relief regions between adjacent ones of the threaded regions, wherein the bone plate is configured to threadedly purchase with the locking bone screw at the threaded regions and not at the relief regions.

7. The bone plate as recited in claim 6, wherein the collection recess is defined by a collection surface that is recessed radially outward with respect to the at least one threaded region.

8. The bone plate as recited in claim 7, wherein the threaded internal locking surface defines a relief recess at each of the relief regions, wherein the relief recesses circumferentially interrupt the at least one thread so as to define a plurality of thread segments, and axially aligned ones of the thread segments combine to define a plurality of threaded columns that are configured to threadedly purchase with the locking bone screw.

9. The bone plate as recited in claim 8, wherein the collection surface interrupts the thread segments of the columns along the axial direction.

10. The bone plate as recited in claim 9, wherein the collection recess is open to adjacent ones of the relief recesses.

11. The bone plate as recited in claim 9, wherein the threaded internal locking surface defines relief surfaces that at least partially define the relief recesses, and the collection surface has a radial depth that is greater than that of circumferentially outer portions of the relief surfaces, and less than that of circumferentially middle portions of the relief surfaces that are disposed circumferentially between the circumferential outer portions of the relief surfaces.

12. The bone plate as recited in claim 9, wherein the collection surface defines an axial length at least twice a pitch of each of the thread segments.

13. The bone plate as recited in claim 8, wherein the collection recess has a radial depth greater than a maximum height of the thread segments.

14. The bone plate as recited in claim 7, wherein the collection surface defines an axially inner end and an axially outer end, and the axially inner end is offset with respect to the axially outer end in a radially inward direction toward the central hole axis.

15. The bone plate as recited in claim 14, wherein each of the axially outer end and the axially inner end is spaced from the central hole axis a respective constant distance along an entire length of the collection recess.

16. The bone plate as recited in claim 7, wherein the collection surface is oriented along a plane that is oriented perpendicular to the central hole axis.

17. A bone fixation system comprising the bone plate as recited in claim 1, and the locking bone screw.

18. A bone plate configured to receive a locking bone screw, the bone plate comprising:
    an inner surface configured to face the underlying bone, and an outer surface opposite the inner surface along an axial direction; and
    a threaded internal locking surface that extends between the outer surface and the inner surface so as to define a locking hole that is oriented along a central hole axis, wherein the threaded internal locking surface defines a collection cavity disposed between the outer surface and the inner surface,
    wherein the collection cavity is configured as a collection recess that is swept circumferentially about the central hole axis, and the collection cavity is configured to collect a shaving that is produced from one of the bone plate and the locking bone screw while the locking bone screw is threadedly mated with the bone plate,
    wherein the collection recess is defined by a collection surface that is recessed radially outward with respect to the at least one threaded region,
    wherein the at least one thread is configured to threadedly purchase with the locking bone screw when the locking bone screw is oriented at an angle relative to the central hole axis within a range of angles at which the locking bone screw is configured to threadedly purchase with the at least one thread,
    wherein the threaded internal locking surface defines a plurality of threaded regions that carry the at least one thread, and further defines a plurality of relief regions between adjacent ones of the threaded regions, wherein the bone plate is configured to threadedly purchase with the locking bone screw at the threaded regions and not at the relief regions,
    wherein the internal surface defines a relief recess at each of the relief regions, wherein the relief recesses circumferentially interrupt the at least one thread so as to define a plurality of thread segments, and axially aligned ones of the thread segments combine to define a plurality of threaded columns that are configured to threadedly purchase with the locking bone screw,
    wherein the collection surface interrupts the thread segments of the columns along the axial direction, and
    wherein the threaded internal locking surface defines relief surfaces that at least partially define the relief recesses, and the collection surface has a radial depth that is greater than that of circumferentially outer portions of the relief surfaces, and less than that of circumferentially middle portions of the relief surfaces that are disposed circumferentially between the circumferential outer portions of the relief surfaces.

19. A bone plate configured to receive a locking bone screw, the bone plate comprising:

an inner surface configured to face the underlying bone, and an outer surface opposite the inner surface along an axial direction; and a threaded internal locking surface that extends between the outer surface and the inner surface so as to define a locking hole that is oriented along a central hole axis, wherein the threaded internal locking surface defines a collection cavity disposed between the outer surface and the inner surface, wherein the collection cavity is configured to collect a shaving that is produced from one of the bone plate and the locking bone screw while the locking bone screw is threadedly mated with the bone plate, wherein the collection cavity is configured as a collection recess that is swept circumferentially about the central hole axis, and the collection recess is defined by a collection surface that is recessed radially outward with respect to the at least one threaded region, wherein the at least one thread is configured to threadedly purchase with the locking bone screw when the locking bone screw is oriented at an angle relative to the central hole axis within a range of angles at which the locking bone screw is configured to threadedly purchase with the at least one thread, wherein the threaded internal locking surface defines a plurality of threaded regions that carry the at least one thread, and further defines a plurality of relief regions between adjacent ones of the threaded regions, wherein the bone plate is configured to threadedly purchase with the locking bone screw at the threaded regions and not at the relief regions, wherein the threaded internal locking surface defines a relief recess at each of the relief regions, wherein the relief recesses circumferentially interrupt the at least one thread so as to define a plurality of thread segments, and axially aligned ones of the thread segments combine to define a plurality of threaded columns that are configured to threadedly purchase with the locking bone screw, and wherein the collection surface interrupts the thread segments of the columns along the axial direction, and the collection surface defines an axial length at least twice a pitch of each of the thread segments.

* * * * *